US010473673B2

(12) United States Patent
McGrane et al.

(10) Patent No.: US 10,473,673 B2
(45) Date of Patent: Nov. 12, 2019

(54) METHODS FOR INCREASING PALATABILITY OF PET FOODSTUFF

(71) Applicant: MARS, INCORPORATED, McLean, VA (US)

(72) Inventors: Scott Joseph McGrane, Leicestershire (GB); Andrew John Taylor, Leicestershire (GB); Matthew Ronald Gibbs, Leicestershire (GB); Richard Masten Fine, Oradell, NJ (US); Boris Klebansky, Oradell, NJ (US)

(73) Assignee: MARS, INCORPORATED, McLean, VA (US)

( * ) Notice: Subject to any disclaimer, the term of this patent is extended or adjusted under 35 U.S.C. 154(b) by 0 days.

(21) Appl. No.: 16/246,091

(22) Filed: Jan. 11, 2019

(65) Prior Publication Data

US 2019/0187158 A1    Jun. 20, 2019

Related U.S. Application Data

(62) Division of application No. 14/898,321, filed as application No. PCT/GB2014/000233 on Jun. 13, 2014, now Pat. No. 10,222,387.

(30) Foreign Application Priority Data

Jun. 14, 2013 (GB) .................................. 1310664.6

(51) Int. Cl.
  *G01N 33/74* (2006.01)
  *C07K 14/705* (2006.01)
  *G16C 20/60* (2019.01)
  *G16B 35/00* (2019.01)
  *C07C 53/126* (2006.01)
  *C07C 57/03* (2006.01)
  *G01N 33/566* (2006.01)

(52) U.S. Cl.
  CPC ........... *G01N 33/74* (2013.01); *C07C 53/126* (2013.01); *C07C 57/03* (2013.01); *C07K 14/705* (2013.01); *C07K 14/70596* (2013.01); *G01N 33/566* (2013.01); *G16B 35/00* (2019.02); *G16C 20/60* (2019.02); *C07K 2319/00* (2013.01); *G01N 2333/70596* (2013.01); *G01N 2333/726* (2013.01)

(58) Field of Classification Search
  None
  See application file for complete search history.

(56) References Cited

U.S. PATENT DOCUMENTS

| | | |
|---|---|---|
| 5,011,912 A | 4/1991 | Hopp et al. |
| 8,008,525 B2 | 8/2011 | Fukatsu et al. |
| 8,299,117 B2 | 10/2012 | Shi et al. |
| 8,399,204 B2 | 3/2013 | Sekiya et al. |
| 2007/0059297 A1 | 3/2007 | Waldron et al. |
| 2008/0004227 A1 | 1/2008 | Hirasawa et al. |
| 2008/0160033 A1 | 7/2008 | Ito et al. |
| 2008/0299270 A1 | 12/2008 | Damak et al. |
| 2014/0248695 A1 | 9/2014 | Bovolenta et al. |
| 2016/0209430 A1 | 7/2016 | McGrane et al. |

FOREIGN PATENT DOCUMENTS

| | | |
|---|---|---|
| JP | 2005325055 | 11/2005 |
| RU | 2 340 213 C2 | 12/2008 |
| RU | 2 423 878 C2 | 7/2011 |
| WO | 2007134613 | 11/2007 |
| WO | 2009125804 A1 | 10/2009 |
| WO | 2011159297 | 12/2011 |

OTHER PUBLICATIONS

Uniprot: "Sequence UPI00004BCC30", [online], Dec. 9, 2004, [*], <URL: http://www.uniprot.org/uniparc/UPI00004BCC30>, 2 pgs.
Uniprot: "Sequence UPI00005A4EBB", [online], Apr. 26, 2012[*], <URL: http://www.uniprot.org/uniparc/UPI00005A4EBB, 1 pg.
Uniprot: "Sequence UPI00005A4EBB", [online], Jun. 21, 2018, [*], <URL: http://www.uniprot.org/uniparc/UPI00005A4EBB, 2 pgs.
Uniprot: "Sequence UPI0002988ED2", [online], Nov. 7, 2012, [*] <URL: http://www.uniprot.org/uniparc/UPI0002988ED2> 1 pg.
Uniprot: "Sequence UPI0002989000", [online], Nov. 7, 2012, [*] <URL: http://www.uniprot.org/uniparc/UPI0002989000>, 2 pgs.
Uniprot: "Sequence UPI0002989000", [online],Jun. 21, 2018, [*] <URL: http://www.uniprot.org/uniparc/UPI0002989000>, 2 pgs.
"XP_003982755.1, CD36 Protein with SEQ ID No. 3 Feb. 15, 2013", Retrieved from: https://www.ncbi.nlm.nih.gov/protein/410952168?sat=18&satkey=3322721, 1 page, Feb. 15, 2013.
Altschul, et al., "Basic Local Alignment Search Tool", J. Mol. Biol., Oct. 1990, 215, 403-410.
Altschul, et al., "Gapped BLAST and PSI-BLAST: A New Generation of Protein Database Search Programs", Nucleic Acids Research, Sep. 1997, vol. 25, No. 17, pp. 3389-3402.
Cartoni, et al., "Taste Preference for Fatty Acids is Mediated by GPR40 and GPR120", Journal of Neuroscience, vol. 30, No. 25, pp. 8376-8382 (Jun. 23, 2010).
Di Palma, et al., "M3Z0H4_MUSPF", May 1, 2013 (May 1, 2013), XP055472512, Retrieved from the Internet: URL: http://www.uniprot.org/uniprot/M3Z0H4.txt?version=2 [retrieved on May 4, 2018],2 pgs., Jan. 5, 2013.
Fushiki, Nutritional physiological study regarding oil preference, Heisei 25 (2013), The Proceedings of the Japan Society for Bioscience, Biotechnology, and Agrochemistry Prize Winner Lecture, Japan, 2013, 8 pgs.(with translation).
Gaillard, et al., "The Gustatory Pathway is Involved in CD36-Mediated Orosensory Perception of Long-Chain Fatty Acids in the Mouse", The FASEB Journal, May 2008, 2(5):1458-1468.

(Continued)

*Primary Examiner* — John D Ulm
(74) *Attorney, Agent, or Firm* — Baker Botts L.L.P.

(57) ABSTRACT

The present invention relates to a method of identifying a compound that binds to or modulates the activity of one or more polypeptides encoding one or more receptors that are involved in the detection and perception of fatty acids.

12 Claims, 28 Drawing Sheets

Specification includes a Sequence Listing.

(56) References Cited

OTHER PUBLICATIONS

Galindo, et al., "G-Protein-Coupled Receptors in Human Fat Taste Perception", Chem. Senses, 37:123-139, Feb. 2012.

Hara, "Novel Selective Ligands for Free Fatty Acid Receptors GPR120 and GPR40", Naunyn-Schmied Arch. Pharmacol. (Sep. 2009), 380:247-255.

Hirasawa, et al., Free fatty acid receptors and drug discovery, Ligand search for fatty acid receptors, Clarification and drug discovery application of a physiological function, Jrnl of Clinical and Experimental Medicine, Japan,May 29, 2010, 233(9), p. 755-760 (Abstract only).

Karlin, et al., "Applications and Statistics for Multiple High-Scoring Segments in Molecular Sequences", Proc. Natl. Acad. Sci. USA vol. 90 pp. 5873-5877, Jun. 1993.

Karlin, et al., "Methods for Assessing the Statistical Significance of Molecular Sequence Features by Using General Scoring Schemes", Proc. Natl. Acad. Sci. USA, vol. 87, pp. 2264-2268, Mar. 1990.

Kuda, "Lysine 164 of CD36 is Important for Fatty Acid Uptake and Signaling to Calcium", J. Biol. Chem., Apr. 2013, 19 pages.

Martin, et al., "The Lipid-Sensor Candidates CD36 and GPR120 are Differentially Regulated by Dietary Lipids in Mouse Taste Buds: Impact on Spontaneous Fat Preference", PLoS One, Aug. 2011, 6(8):e24014, 1-10.

Myers, et al., "Optical Alignments in Linear Space", Comput. Appl. Biosci., Mar. 1988, 4(1):11-7, Abstract Only (1 pg.).

Nelson, et al., "Mammalian Sweet Taste Receptors", Cell, vol. 106, p. 381-390, Aug. 10, 2001.

Pearson, et al., "Improved Tools for Biological Sequence Comparison", Proc. Natl. Acad. Sci. USA, 85:2444-8, Apr. 1988.

Pontius, et al., "Uniprot:M2WCE6", Genome Research, May 1, 2013, XP55472511, Retrieved from the Internet: URL: http://www.uniprot.org/uniprot/M3WCE6 [retrieved on May 4, 2018], 2 pgs., Jan. 5, 2013.

Shimpukade, et al., "Discovery of a Potent and Selective GPR120 Agonist", Journal of Medicinal Chemistry, vol. 55, No. 9, pp. 4511-4515 (Apr. 23, 2012).

Sun, et al., "Structure-Activity Relationships of GPR120 Agonists Based on a Docking Simulation", Molecular Pharmacology, vol. 78, No. 5, Nov. 1, 2010, pp. 804-810, ZP055122562.

Suzuki, et al., "Identification of G Protein-Coupled Receptor 120 Selective Agonists Derived from PPAR-gamma Agonists", J. Med. Chem., Nov. 2008, 51, 7640-7644.

Torelli, et al., "Advance and Adam: two algorithms for the analysis of global similarity between homologous informational sequences", Comput. Appl. Biosci., 10:3-5 (Feb. 1994).

Figure 1 – SEQ ID NO:1.

Feline GPR120 Protein Sequence (361aa)

MSPECAQAAGTGSPRSLERANRTRFPFFSDVKGDHRLVLTAVETVVLALIFAVSLLGNV
CALVLVARRRRRGTTACLVLNLFCADLLFTSAIPPVLAVRWTEAWLLGPVACHLLFYVM
SLSGSVTILTLAAVSLERMVCIVRLQRGVRGLGRRARAALLALIWGYSALAALPLCVFF
QVVPQRLSGRDQEIPICTLSWPSIAGEISWDVSFVTLNFLMPGLLIVISYSKILQITKA
SRKRLTVNLASSESHHIRVSQQDFRLFRTLFLLMISFFIMWSPIIITILLILIQNFKQD
LVIWPSLFFWVVAFTFANSALNPILYNMSLFRNEWRKIFHCFFYPEKGAMFTDTSVRRN
DLSVISN

Figure 2 – SEQ ID NO:2.

Feline GPR120 Coding Transcript Sequence

ATGTCCCTGAGTGCGCGCAGGCGGCGGGCACTGGGTCCCGCGCAGCCTGGAGCGGGC
CAACCGCACCCGCTTCCCATTCTTCTCCGACGTCAAGGGAGACCACCGGCTGGTGCTGA
CCGCTGTGGAGACGGTCGTGCTGGCGCTCATCTTCGCGGTGTCGCTGTTGGGCAACGTG
TGCGCCTTGGTGCTGGTGGCGCGCCGACGGCGCCGCGGCACCACCGCCTGCCTGGTGCT
CAACCTTTTCTGCGCGGACCTGCTCTTCACCAGCGCCATCCCGCCCGTGCTGGCTGTGC
GATGGACTGAGGCCTGGCTGCTGGGCCCGGTCGCCTGCCACCTGCTCTTCTACGTGATG
AGCTTGAGCGGCAGCGTCACCATCCTCACGCTGGCGGCCGTCAGCCTGGAGCGCATGGT
GTGCATCGTTCGCCTGCAGCGGGCGTGCGGGCCTGGGGCGGCGGGCGAGGCCGCGC
TGCTGGCGCTCATCTGGGCTACTCGGCGCTGGCCGCGCTGCCCCTCTGCGTCTTCTTC
CAAGTCGTTCCGCAGCGGCTCTCCGGTCGGGACCAGGAAATTCCGATTTGCACACTGAG
TTGGCCCAGCATCGCTGGAGAAATCTCCTGGGATGTGTCGTTTGTTACTTTGAACTTTT
TGATGCCGGGATTGCTCATTGTGATCAGCTACTCCAAGATTTTACAGATCACAAAGGCA
TCAAGGAAAAGGCTCACGGTGAACCTGGCTTCCTCGGAGAGCCACCATATCCGCGTGTC
CCAGCAGGACTTCCGGCTCTTCCGTACCCTCTTCCTGCTCATGATCTCCTTCTTCATTA
TGTGGAGCCCCATCATCATCACCATCCTCCTCATCTTGATCCAGAATTTCAAGCAGGAC
CTGGTCATCTGGCCATCCCTCTTCTTCTGGGTGGTGGCCTTCACGTTTGCCAACTCAGC
CCTGAACCCCATTCTCTATAACATGTCACTGTTTAGGAATGAATGGAGGAAAATTTTCC
ATTGCTTCTTCTACCCAGAAAGGGAGCCATGTTTACAGATACATCTGTCAGAAGAAAT
GATCTGTCCGTTATTTCCAACTAA

Figure 3 – SEQ ID NO:3.

Feline CD36 Protein Sequence (472aa)

MGCDRNCGLIAGAVIGAVLAVFGGILMPVGDMLIERTIKKEVVLEEGTIAYQNWVKTGT
EVYRQFWIYDVQNPQEVVANSSKIKVKQRGPYTYRVRYLAKKNITHDPETHTVSFLQPN
AAIFEPSLSAGTENDTWTVLNLAVAAAPHLYPNAFVQVVLNSLIKKSKSSMFQKRTVKE
LLWGYKDPFLSLVPYPISTTVGVFFPYNNTADGVYTVFSGKDNISQVAIIDTYKGKKNL
SYWPSYCDMINGTDAASFPPFVEKTRVLRFFSSDICRSIYAVFGAEINLKGIPVYRFVL
PSMAFASPLQNPDNHCFCTETVISNNCTSYGVLDIGRCKEGKPVYISLPHFLHASPDIA
EPIEGLTPNEDEHSTYLDVEPITGFTLRFAKRLQINILVKPAKKIEALKGLKRNYIVPI
LWLNETGTIGDEKAEMFRKRVTGKINLLGLVEITLLSVGVVMFVAFMISYCACRSKKVK

Figure 4 – SEQ ID NO:4.

Feline CD36 Coding Transcript Sequence

ATGGGCTGTGACCGAAACTGTGGGCTCATTGCTGGTGCTGTCATTGGTGCAGTCCTGGC
CGTGTTTGGAGGCATTCTAATGCCAGTCGGAGACATGCTTATTGAGAGGACAATCAAAA
AGGAGGTTGTACTCGAGGAAGGTACCATTGCTTATCAAAATTGGGTTAAAACAGGCACA
GAAGTTTACAGACAGTTTTGGATCTATGATGTGCAAAACCCACAGGAAGTGGTAGCTAA
TAGCAGCAAAATTAAAGTTAAACAAAGAGGTCCTTACACGTACAGAGTTCGTTATCTAG
CCAAAAAAATATAACCCACGATCCTGAGACCCACACAGTCTCTTTTCTTCAGCCCAAT
GCGGCCATCTTCGAGCCTTCACTATCAGCTGGAACAGAGAATGACACTTGGACTGTTCT
CAATCTGGCTGTAGCAGCTGCACCCCATCTCTACCCAAATGCATTTGTTCAAGTGGTAC
TCAATTCACTTATCAAAAAGTCAAAATCTTCCATGTTTCAAAAAAGAACTGTGAAAGAG
CTCTTGTGGGCTATAAAGATCCGTTCTTGAGTTTGGTTCCATATCCTATTTCCACGAC
AGTTGGTGTGTTTTTTCCTTACAACAACACTGCAGATGGAGTTTATACAGTTTTCAGTG
GGAAAGACAACATCAGCCAAGTTGCCATAATTGACACTTACAAAGGTAAAAAGAATCTC
TCCTATTGGCCAAGTTATTGTGACATGATTAATGGTACAGACGCAGCCTCATTTCCACC
TTTTGTTGAGAAGACGCGAGTGTTACGTTTCTTTTCTTCTGACATTTGCAGGTCAATCT
ATGCTGTGTTTGGAGCTGAAATTAACCTGAAAGGAATCCCTGTCTATAGATTTGTTCTT
CCATCCATGGCCTTTGCATCTCCACTTCAAAATCCAGATAACCATTGTTTCTGCACAGA
AACCGTTATCTCCAATAATTGTACATCATATGGTGTATTAGACATTGGCAGATGCAAAG
AAGGAAAACCTGTGTATATTTCACTTCCTCATTTTCTACATGCAAGTCCTGATATTGCA
GAACCCATTGAAGGCTTAACTCCAAATGAAGACGAACATAGCACATACTTAGATGTTGA
ACCTATAACTGGATTCACTTTACGATTTGCAAAACGGCTGCAAATCAACATATTGGTCA
AACCAGCAAAGAAATTGAGGCATTAAAGGGTCTTAAGCGGAACTATATTGTGCCTATT
CTTTGGCTTAATGAGACTGGTACCATTGGTGATGAGAAGGCAGAAATGTTTAGAAAAG
AGTGACTGGAAAAATCAACCTTCTTGGCCTGGTAGAAATTACCTTACTCAGTGTTGGCG
TGGTGATGTTTGTTGCTTTTATGATTTCATACTGTGCGTGCAGATCAAAGAAAGTAAAA
TAA

Figure 5 – SEQ ID NO:5.

Canine GPR120 Protein Sequence (361aa)
MSPECAQAPGAGSPRSLERANRTRFPFFSDVKGDHRLVLTAVETVVLALIFAVSLLGNV
CALVLVARRRRGTTACLVLNLFCADLLFTSAIPPVLAVRWTEAWLLGPVACHLLFYVM
SLSGSVTILTLAAVSLERVVCIVRLQRGARGLGRRARAALLALVWGYSALAALPLCVFF
HVVPQRLPGRDQEILICTLAWTSVAGEISWDVSFVTLNFLVPGLLIVISYSKILQITKA
SRKRLTVNLAYSESHHIRVSQQDFRLFRTLFLLMISFFIMWSPIIITILLILIQNFKQD
LVIWPSLFFWVVAFTFANSALNPILYNMSLFRNEWRKIFHCFFYPEKGAMFTDTSVRRN
DLSIIYS Figure 6 – SEQ ID NO:6.

Canine GPR120 Coding Transcript Sequence
ATGTCCCCTGAGTGCGCGCAGGCGCCGGGCGCCGGGTCCCCGCGCAGCCTGGAGCGGGC
CAACCGCACCCGCTTCCCCTTCTTCTCCGACGTCAAGGGCGACCACCGGCTGGTGCTGA
CCGCCGTGGAGACGGTCGTGCTGGCGCTCATCTTCGCGGTGTCGCTGTTGGGCAACGTG
TGCGCCTTGGTGCTGGTGGCGCGCCGACGGCGCCGCGGCACCACCGCCTGCCTGGTGCT
CAACCTCTTCTGCGCCGACCTGCTCTTCACCAGCGCCATCCCGCCCGTGCTGGCCGTGC
GGTGGACCGAGGCCTGGCTGCTGGGCCCGGTCGCCTGCCACCTGCTCTTCTACGTGATG
AGCCTGAGCGGCAGCGTCACCATCCTCACGCTGGCGGCCGTCAGCCTGGAGCGCGTGGT
GTGCATCGTCCGCCTGCAGCGGGGCGCGCGGGGCCTGGGCGGCGGGCGAGGGCCGCGC
TGCTGGCGCTCGTCTGGGCTACTCGGCGCTCGCCGCGCTGCCGCTCTGCGTCTTCTTC
CACGTCGTCCCCAGCGGCTGCCCGGTCGCGACCAGGAAATTCTGATTTGCACACTGGC
TTGGACCAGTGTTGCCGGAGAAATCTCCTGGGACGTGTCGTTTGTTACTTTGAACTTCT
TGGTACCAGGATTGCTCATTGTGATCAGCTACTCCAAAATTTTACAGATCACAAAGGCG
TCAAGGAAAAGGCTCACGGTGAACCTAGCTTACTCAGAGAGCCACCATATCCGCGTGTC
CCAGCAGGACTTCCGGCTCTTCCGCACGCTCTTCCTGCTCATGATCTCCTTCTTCATTA
TGTGGAGCCCCATCATCATCACCATCCTCCTCATCTTGATCCAGAACTTCAAGCAAGAC
TTGGTCATCTGGCCATCCCTCTTCTTCTGGGTGGTGGCATTCACGTTTGCCAACTCGGC
CCTGAACCCCATTCTCTATAACATGTCACTGTTTAGGAATGAATGGAGGAAAATTTTTC
ACTGCTTCTTCTACCCAGAAAAGGGAGCCATGTTTACAGATACATCTGTCAGAAGAAAT
GATCTGTCAATTATTTACAGCTAA Figure 7 – SEQ ID NO:7.

Canine CD36 Protein Sequence (472aa)

MGCDRNCGLIAGAVIGAVLALLGGILMPVGDMLIEKTIKKEVVLEEGTIAFKNWVKTGT
EVYRQFWIFDVQNAQEVVANSSKIKVKQRGPYTYRVRYLAKENITHDTENHLVSFVQPN
GAIFEPSLSVGTEDDTMTVLNLAVAAAPHLYPNAFVQVVLNSLIKKSKSSMFQNRTVKE
LLWGYTDPFLSLVPYPVNTKVGVFYPYNNTVDGVYSVFSGKDNVSQVAIIDTYKGKKNL
SYWPSYCDMINGTDAASFPPFVEKTRVLRFFSSDICRSIYAVFGAEINLKGIPVYRFVL
PSMAFASPLQNPDNHCFCTEKVISNNCTSYGVLDIGKCKEGKPVYISLPHFLHASPDIG
EPIEGLSPNEDEHTTYLDVEPITGFTLRFAKRLQINILVKPAKKIEALKNLKRNYIVPI
LWLNETGTIGDEKAAQFRKQVTGKINLLGLVEIILLTVGVVMFVAFMISYCACRSKGKR

Figure 8- SEQ ID NO:8.

Canine CD36 Coding Transcript Sequence

ATGGGCTGTGACCGCAACTGTGGGCTCATCGCGGGCGCTGTCATCGGGGCAGTGCTCGC
CCTGCTGGGGGGCATTCTGATGCCCGTCGGAGACATGCTGATTGAGAAGACAATCAAGA
AGGAAGTTGTACTTGAAGAAGGTACAATTGCTTTCAAAAATTGGGTTAAAACAGGCACA
GAAGTTTACAGACAGTTTTGGATCTTTGACGTGCAAAATGCACAGGAAGTGGTTGCGAA
CAGCAGCAAAATTAAGGTTAAACAAAGAGGTCCTTACACATACAGAGTTCGTTATCTAG
CCAAAGAAATATAACTCATGACACTGAGAACCACTTAGTCTCTTTTGTCCAGCCCAAC
GGTGCCATCTTTGAACCTTCACTATCTGTTGGAACAGAAGATGACACTATGACCGTTCT
CAATCTGGCTGTAGCAGCTGCACCCCATCTCTATCCAAATGCATTTGTTCAAGTGGTAC
TCAATTCACTTATCAAAAGTCAAAATCGTCTATGTTTCAAAATAGAACTGTGAAAGAG
CTCTTGTGGGCTACACGGATCCATTCTTGAGTTTGGTTCCATACCCTGTTAACACAAA
AGTTGGTGTGTTTATCCTTACAACAACACTGTCGATGGAGTTTATTCAGTTTTCAGTG
GGAAAGACAACGTAAGCCAAGTTGCCATAATTGACACTTACAAAGGTAAAAAGAATCTC
TCCTATTGGCCAAGTTATTGTGACATGATTAATGGTACAGATGCAGCCTCATTTCCACC
TTTTGTAGAGAAGACACGAGTATTGCGTTTCTTTTCCTCTGACATTTGCAGGTCAATCT
ATGCTGTGTTTGGAGCTGAAATTAACCTGAAAGGAATTCCTGTCTATAGATTTGTTCTT
CCATCCATGGCCTTTGCATCTCCACTTCAAAATCCAGATAATCATTGTTTCTGCACAGA
AAAAGTTATCTCAAATAACTGCACATCATATGGTGTGCTAGACATTGGCAAATGCAAAG
AAGGAAAACCTGTGTATATTTCACTTCCTCATTTCTACATGCAAGTCCTGATATTGGA
GAACCTATTGAAGGCTTAAGTCCAAATGAAGATGAACATACCACATACTTAGATGTTGA
ACCTATAACTGGATTCACTTTACGATTTGCAAAACGGCTGCAAATCAACATATTGGTCA
AGCCAGCAAAAAAATTGAAGCATTAAAGAATCTGAAGCGAAACTACATTGTACCTATT
CTTTGGCTTAATGAGACTGGTACCATCGGTGATGAGAAGGCAGCACAGTTCAGAAAACA
AGTGACCGGAAAAATAAACCTCCTTGGCCTGGTAGAAATCATCTTACTCACTGTTGGTG
TGGTGATGTTTGTTGCTTTTATGATTTCATACTGTGCATGCAGATCAAAGGGAAAAGA
TAA

Figure 9 – SEQ ID NO:9.

Human GPR120 Protein Sequence (361aa)
MSPECARAAGDAPLRSLEQANRTRFPFFSDVKGDHRLVLAAVETTVLVLIFAVSLLGNV
CALVLVARRRRGATACLVLNLFCADLLFISAIPLVLAVRWTEAWLLGPVACHLLFYVM
TLSGSVTILTLAAVSLERMVCIVHLQRGVRGPGRRARAVLLALIWGYSAVAALPLCVFF
RVVPQRLPGADQEISICTLIWPTIPGEISWDVSFVTLNFLVPGLVIVISYSKILQITKA
SRKRLTVSLAYSESHQIRVSQQDFRLFRTLFLLMVSFFIMWSPIIITILLILIQNFKQD
LVIWPSLFFWVVAFTFANSALNPILYNMTLCRNEWKKIFCCFWFPEKGAILTDTSVKRN
DLSIISG Figure 10 – SEQ ID NO:10.

Human GPR120 Coding Transcript Sequence (1086nt)

ATGTCCCTGAATGCGCGCGGGCAGCGGGCGACGCGCCCTTGCGCAGCCTGGAGCAAGC
CAACCGCACCCGCTTTCCCTTCTTCTCCGACGTCAAGGGCGACCACCGGCTGGTGCTGG
CCGCGGTGGAGACAACCGTGCTGGTGCTCATCTTTGCAGTGTCGCTGCTGGGCAACGTG
TGCGCCCTGGTGCTGGTGGCGCGCCGACGACGCCGCGGCGCGACTGCCTGCCTGGTACT
CAACCTCTTCTGCGCGGACCTGCTCTTCATCAGCGCTATCCCTCTGGTGCTGGCCGTGC
GCTGGACTGAGGCCTGGCTGCTGGGCCCCGTTGCCTGCCACCTGCTCTTCTACGTGATG
ACCCTGAGCGGCAGCGTCACCATCCTCACGCTGGCCGCGGTCAGCCTGGAGCGCATGGT
GTGCATCGTGCACCTGCAGCGCGGCGTGCGGGGTCCTGGGCGGCGGGCGCGGGCAGTGC
TGCTGGCGCTCATCTGGGGCTATTCGGCGGTCGCCGCTCTGCCTCTCTGCGTCTTCTTC
CGAGTCGTCCCGCAACGGCTCCCCGGCGCCGACCAGGAAATTTCGATTTGCACACTGAT
TTGGCCCACCATTCCTGGAGAGATCTCGTGGGATGTCTCTTTTGTTACTTTGAACTTCT
TGGTGCCAGGACTGGTCATTGTGATCAGTTACTCCAAAATTTTACAGATCACAAAGGCA
TCAAGGAAGAGGCTCACGGTAAGCCTGGCCTACTCGGAGAGCCACCAGATCCGCGTGTC
CCAGCAGGACTTCCGGCTCTTCCGCACCCTCTTCCTCCTCATGGTCTCCTTCTTCATCA
TGTGGAGCCCCATCATCATCACCATCCTCCTCATCCTGATCCAGAACTTCAAGCAAGAC
CTGGTCATCTGGCCGTCCCTCTTCTTCTGGGTGGTGGCCTTCACATTTGCTAATTCAGC
CCTAAACCCCATCCTCTACAACATGACACTGTGCAGGAATGAGTGGAAGAAAATTTTTT
GCTGCTTCTGGTTCCCAGAAAAGGGAGCCATTTTAACAGACACATCTGTCAAAGAAAT
GACTTGTCGATTATTTCTGGCTAA

Figure 11 – SEQ ID NO:11.

Human CD36 Protein Sequence (472aa)

MGCDRNCGLIAGAVIGAVLAVFGGILMPVGDLLIQKTIKKQVVLEEGTIAFKNWVKTGT
EVYRQFWIFDVQNPQEVMMNSSNIQVKQRGPYTYRVRFLAKENVTQDAEDNTVSFLQPN
GAIFEPSLSVGTEADNFTVLNLAVAAASHIYQNQFVQMILNSLINKSKSSMFQVRTLRE
LLWGYRDPFLSLVPYPVTTTVGLFYPYNNTADGVYKVFNGKDNISKVAIIDTYKGKRNL
SYWESHCDMINGTDAASFPPFVEKSQVLQFFSSDICRSIYAVFESDVNLKGIPVYRFVL
PSKAFASPVENPDNYCFCTEKIISKNCTSYGVLDISKCKEGRPVYISLPHFLYASPDVS
EPIDGLNPNEEEHRTYLDIEPITGFTLQFAKRLQVNLLVKPSEKIQVLKNLKRNYIVPI
LWLNETGTIGDEKANMFRSQVTGKINLLGLIEMILLSVGVVMFVAFMISYCACRSKTIK

Figure 12 – SEQ ID NO:12.

Human CD36 Coding Transcript Sequence (1419nt)

ATGGGCTGTGACCGGAACTGTGGGCTCATCGCTGGGCTGTCATTGGTGCTGTCCTGGC
TGTGTTTGGAGGTATTCTAATGCCAGTTGGAGACCTGCTTATCCAGAAGACAATTAAAA
AGCAAGTTGTCCTCGAAGAAGGTACAATTGCTTTTAAAAATTGGGTTAAAACAGGCACA
GAAGTTTACAGACAGTTTTGGATCTTTGATGTGCAAAATCCACAGGAAGTGATGATGAA
CAGCAGCAACATTCAAGTTAAGCAAAGAGGTCCTTATACGTACAGAGTTCGTTTTCTAG
CCAAGGAAAATGTAACCCAGGACGCTGAGGACAACACAGTCTCTTTCCTGCAGCCCAAT
GGTGCCATCTTCGAACCTTCACTATCAGTTGGAACAGAGGCTGACAACTTCACAGTTCT
CAATCTGGCTGTGGCAGCTGCATCCCATATCTATCAAAATCAATTTGTTCAAATGATCC
TCAATTCACTTATTAACAAGTCAAAATCTTCTATGTTCCAAGTCAGAACTTTGAGAGAA
CTGTTATGGGCTATAGGGATCCATTTTGAGTTTGGTTCCGTACCCTGTTACTACCAC
AGTTGGTCTGTTTTATCCTTACAACAATACTGCAGATGGAGTTTATAAAGTTTTCAATG
GAAAAGATAACATAAGTAAAGTTGCCATAATCGACACATATAAAGGTAAAAGGAATCTG
TCCTATTGGGAAAGTCACTGCGACATGATTAATGGTACAGATGCAGCCTCATTTCCACC
TTTTGTTGAGAAAAGCCAGGTATTGCAGTTCTTTTCTTCTGATATTTGCAGGTCAATCT
ATGCTGTATTTGAATCCGACGTTAATCTGAAAGGAATCCCTGTGTATAGATTTGTTCTT
CCATCCAAGGCCTTTGCCTCTCCAGTTGAAAACCCAGACAACTATTGTTTCTGCACAGA
AAAAATTATCTCAAAAAATTGTACATCATATGGTGTGCTAGACATCAGCAAATGCAAAG
AAGGGAGACCTGTGTACATTTCACTTCCTCATTTTCTGTATGCAAGTCCTGATGTTTCA
GAACCTATTGATGGATTAAACCCAAATGAAGAAGAACATAGGACATACTTGGATATTGA
ACCTATAACTGGATTCACTTTACAATTTGCAAACGGCTGCAGGTCAACCTATTGGTCA
AGCCATCAGAAAAAATTCAAGTATTAAAGAATCTGAAGAGGAACTATATTGTGCCTATT
CTTTGGCTTAATGAGACTGGGACCATTGGTGATGAGAAGGCAAACATGTTCAGAAGTCA
AGTAACTGGAAAAATAAACCTCCTTGGCCTGATAGAAATGATCTTACTCAGTGTTGGTG
TGGTGATGTTTGTTGCTTTTATGATTTCATATTGTGCATGCAGATCGAAAACAATAAAA
TAA

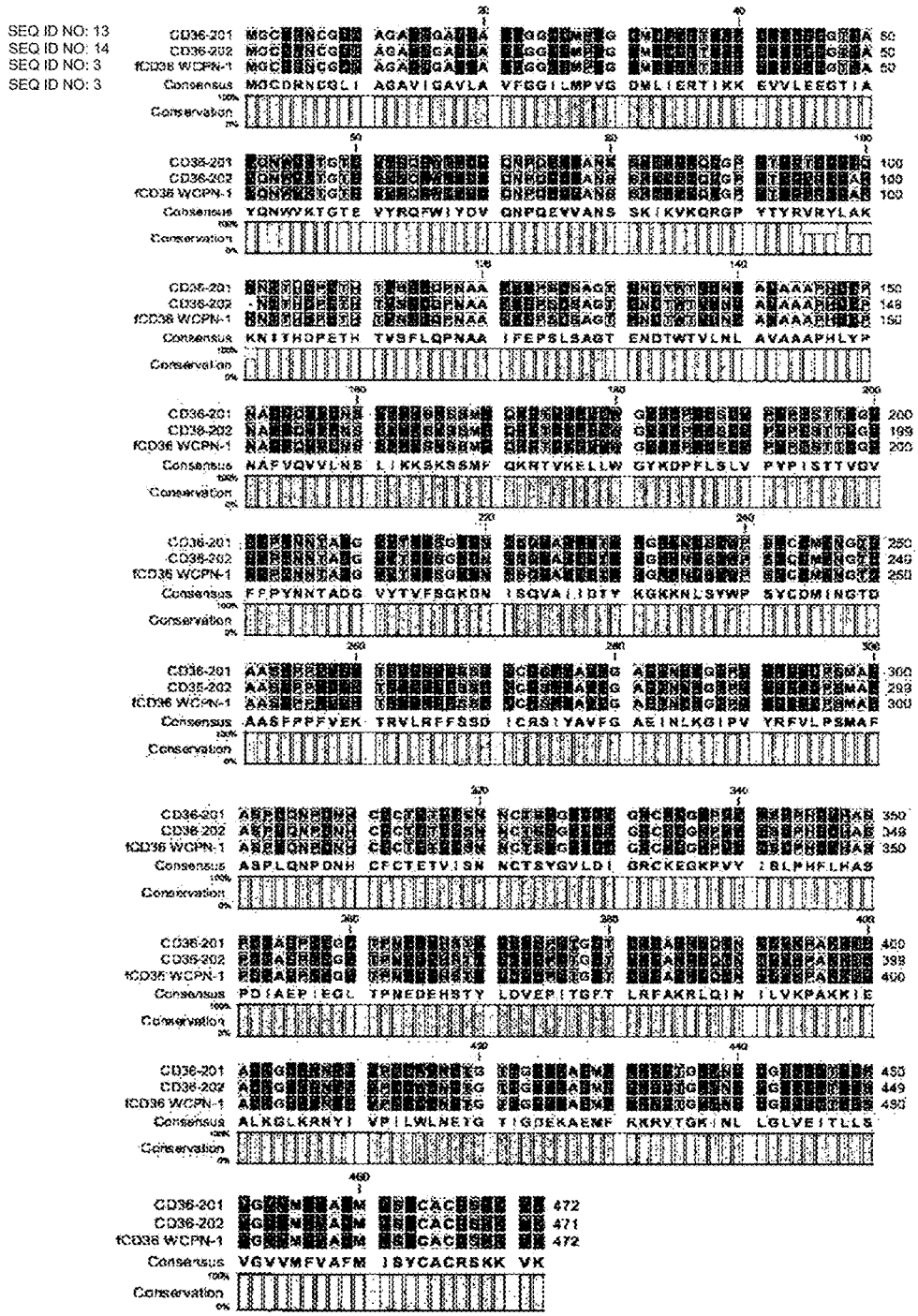
Figure 13 - Sequence alignment of published feline CD36 sequence and that of SEQ ID NO:3

Figure 14 – Feline dose response curve for oleic acid.
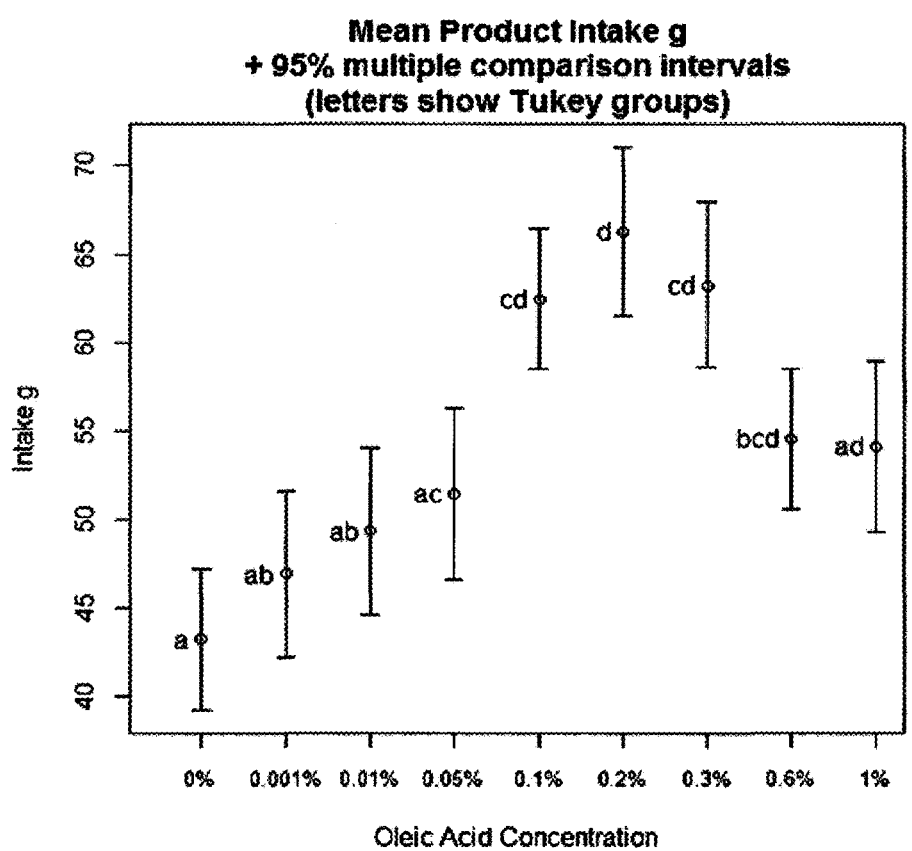

Figure 15 – Feline dose response curve for linoleic acid.
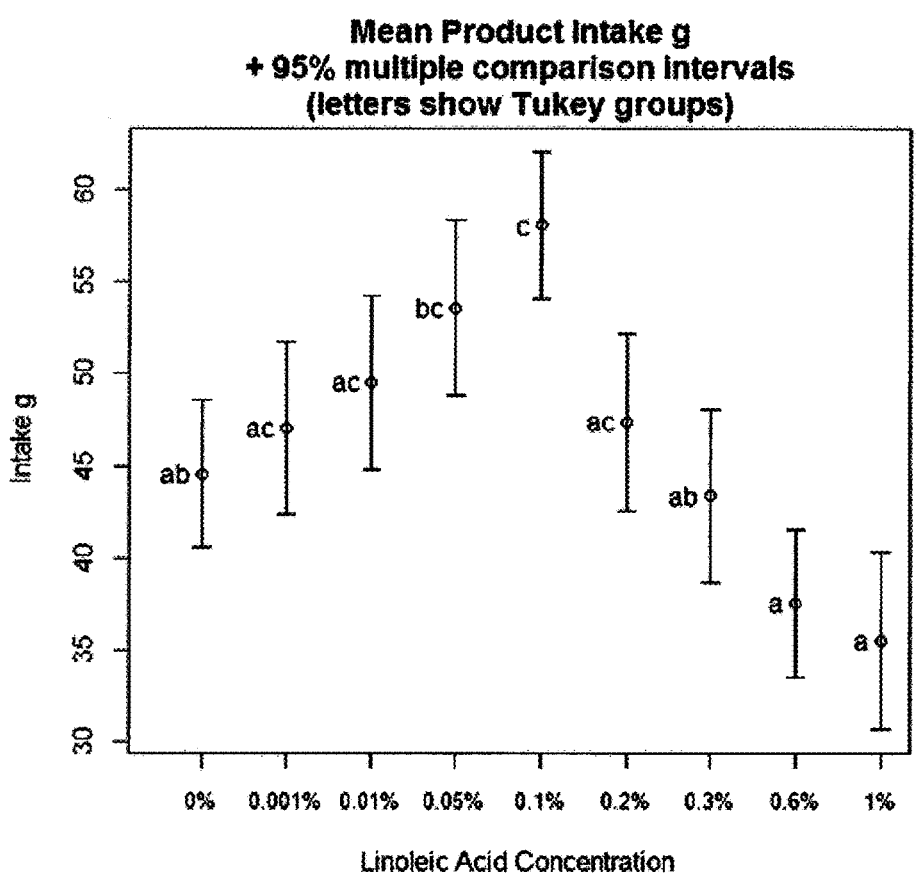

Figure 16 — Feline dose response curve for lauric acid.
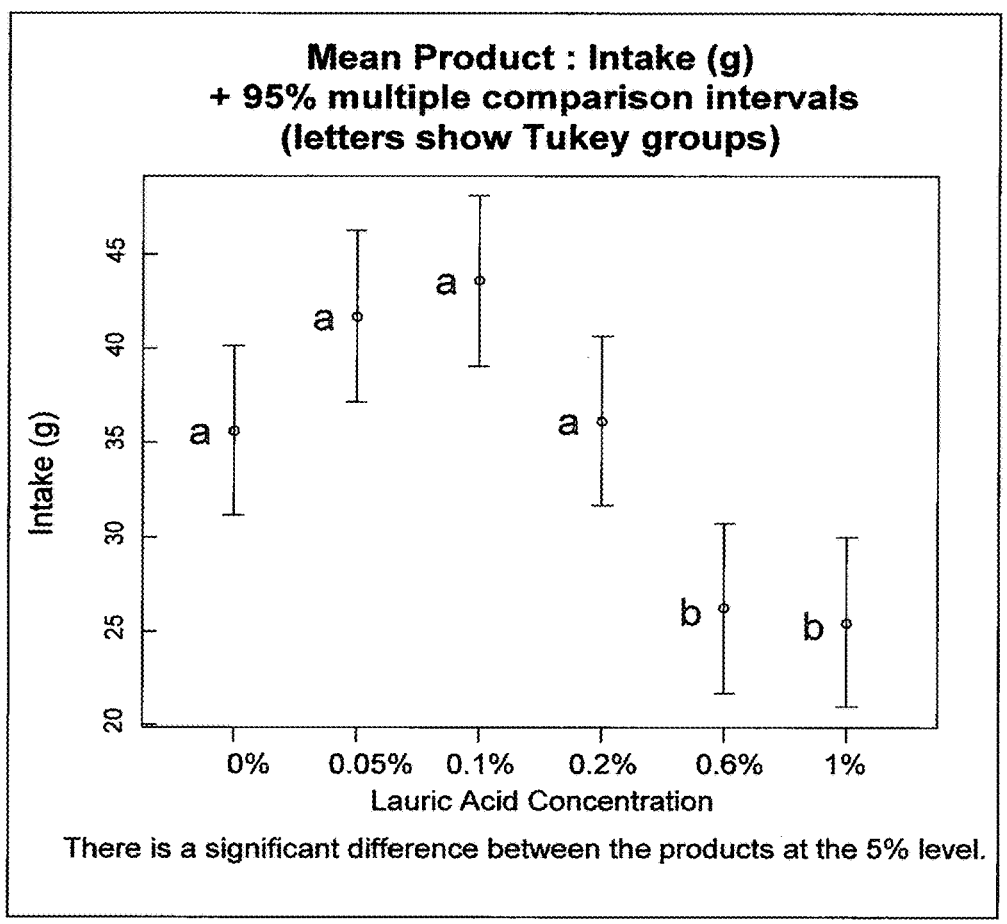

Figure 17 – Feline dose response curve for palmitic acid.
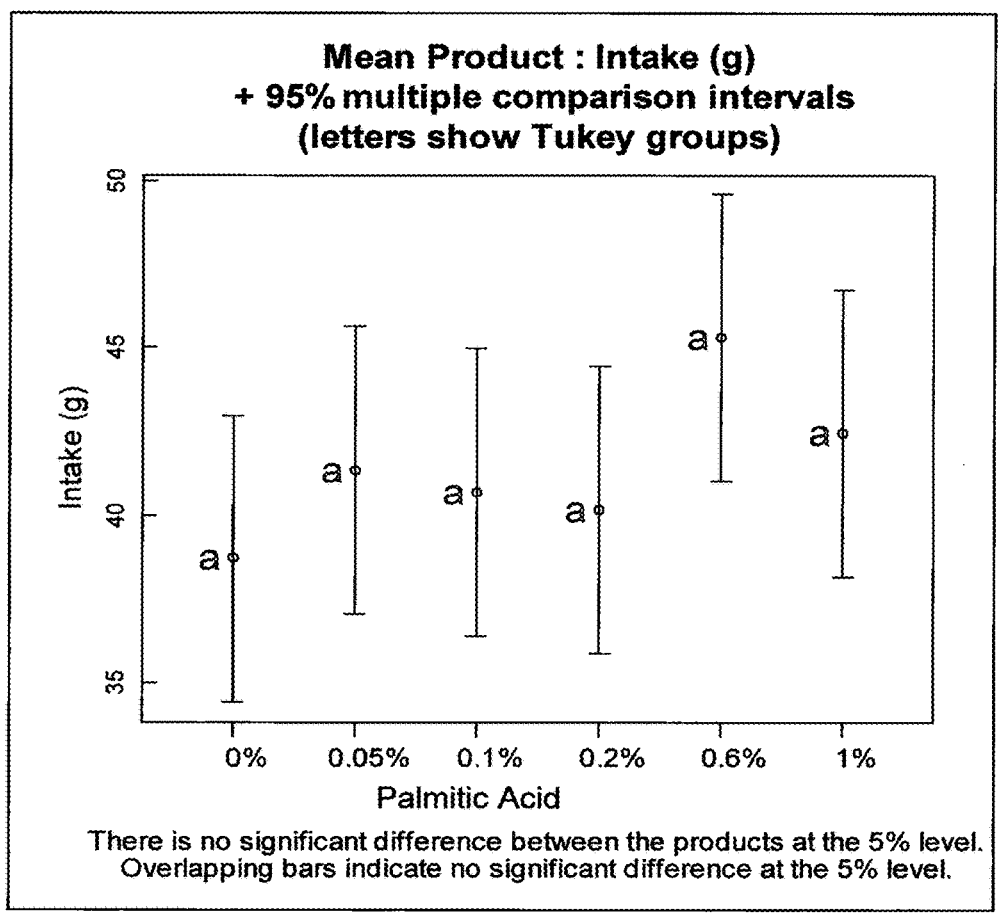

Figure 18 – Canine dose response curves for linoleic acid.
BREED 1:
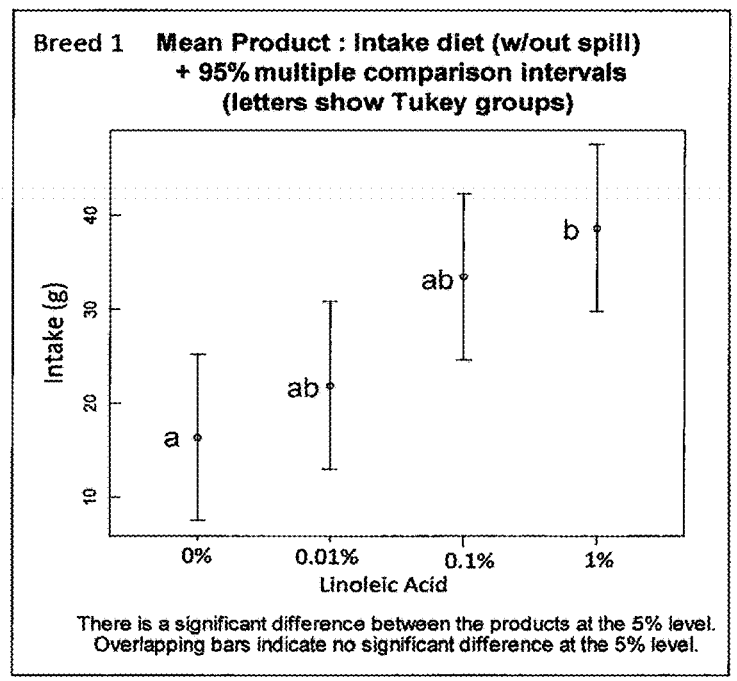
BREED 2:
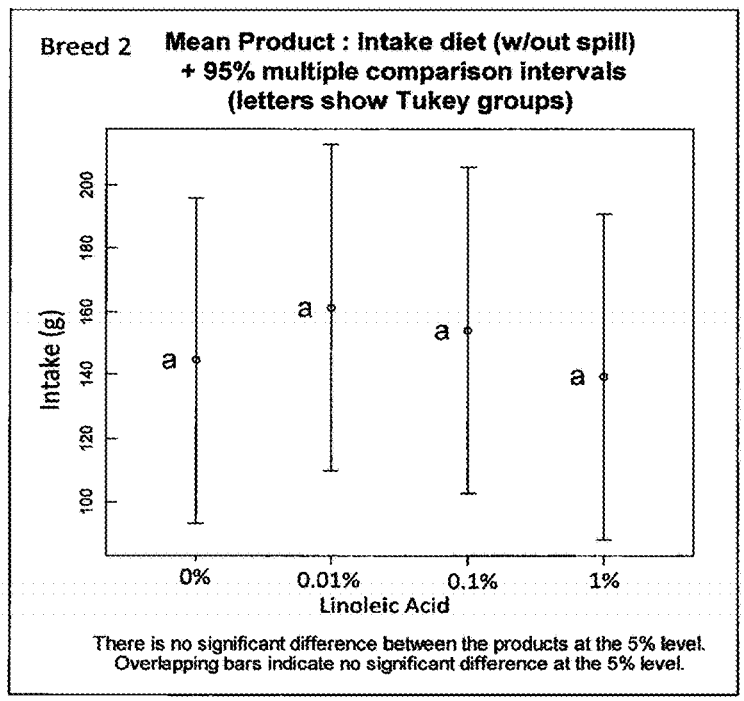

BREED 1:
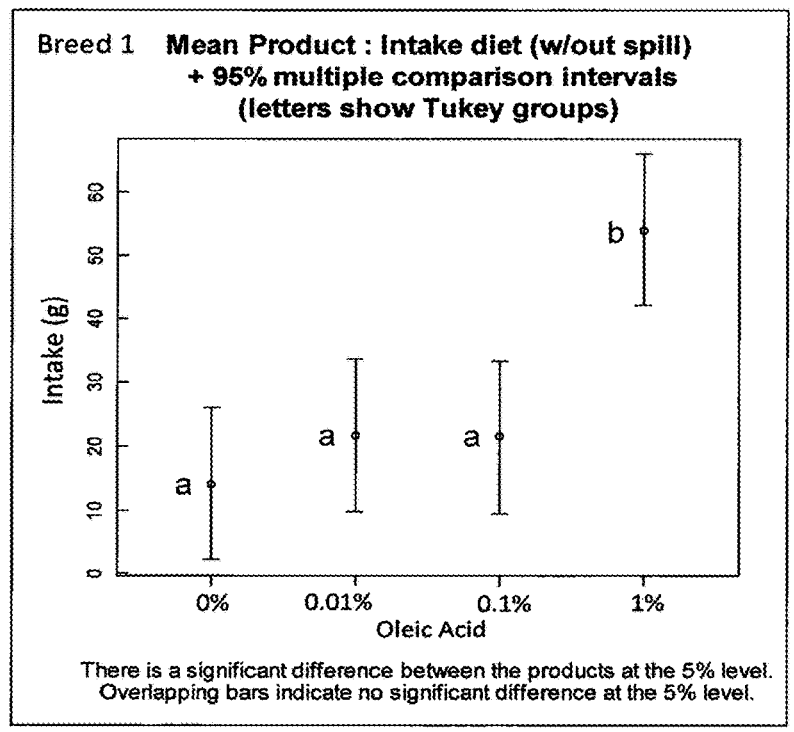
BREED 2:
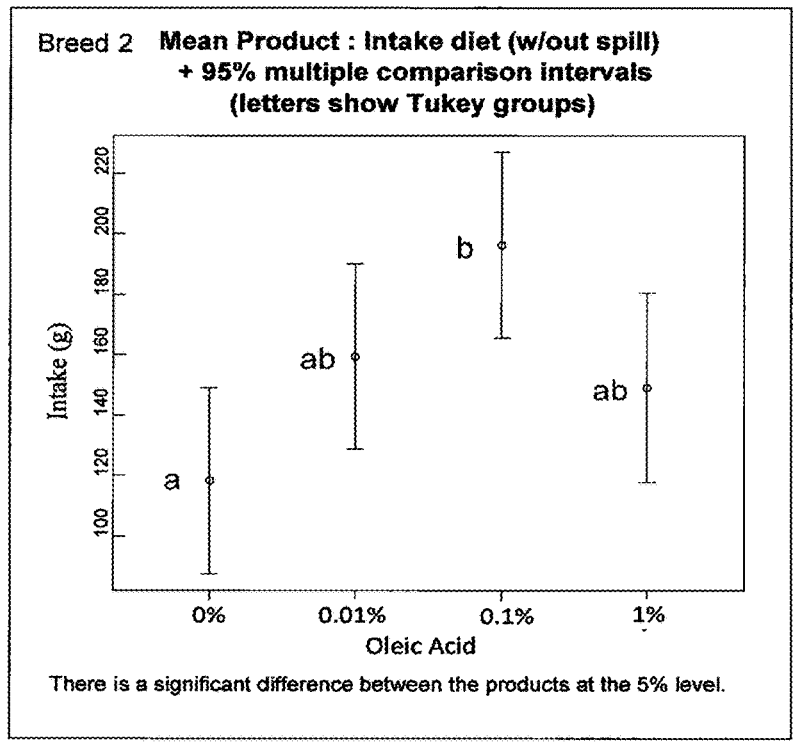

Figure 21—Predicted structure of human CD36 receptor.
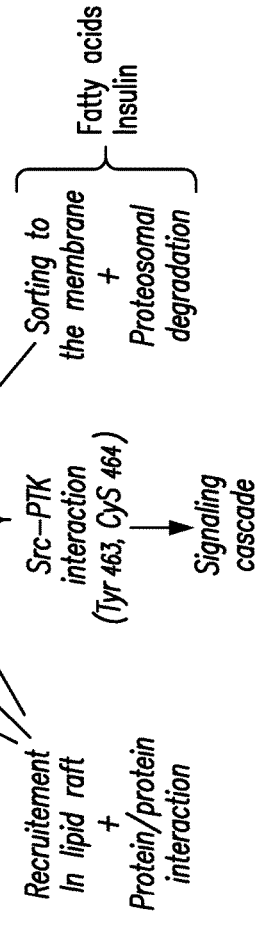
Fig 1. Main structural features of human CD36. AGE, advanced-glycation end products; LCFA, long-chain fatty acids; OxLDL, oxidized low density lipoproteins; Src-PTK, Src protein tyrosine kinases. Adapted from Refs. [10,75,76].

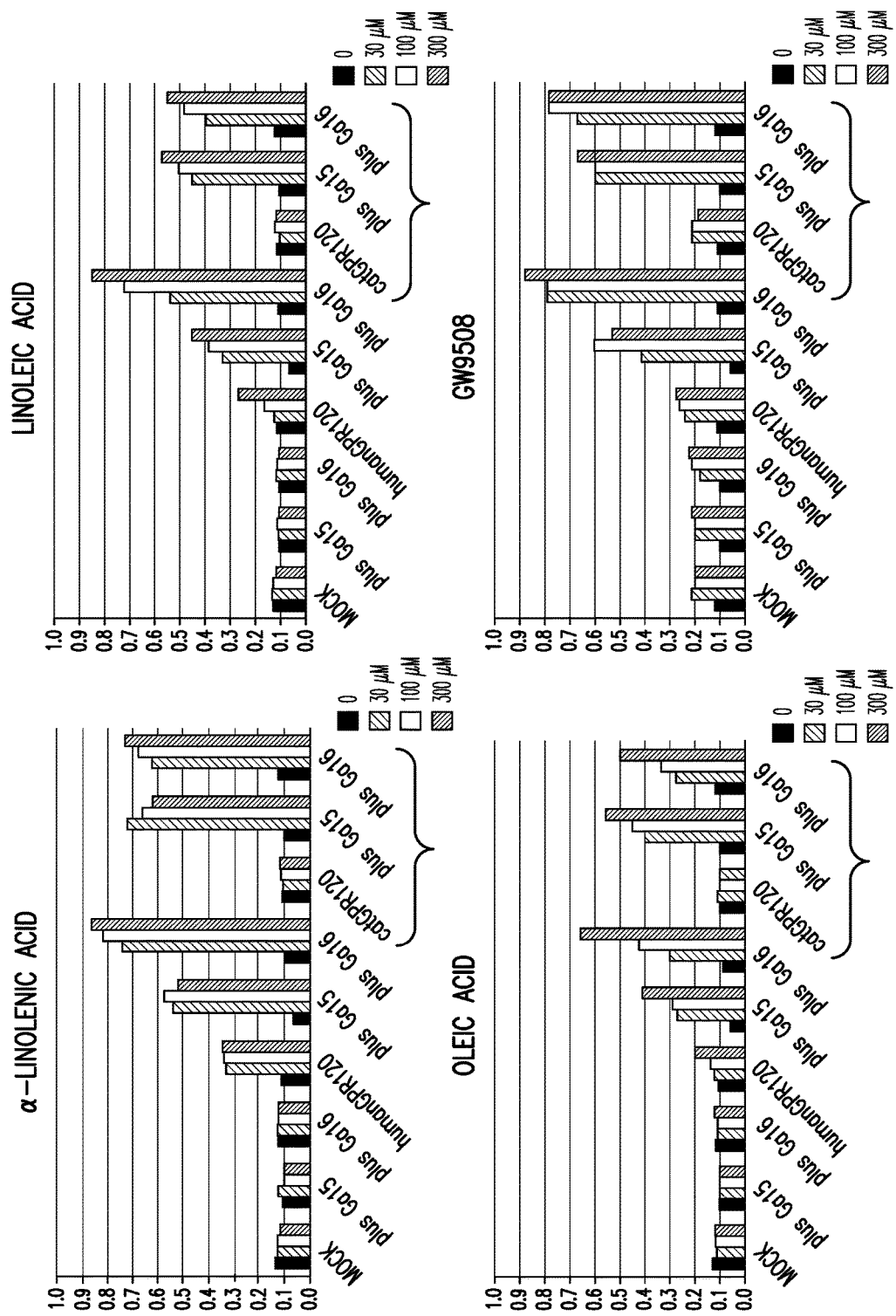
Figure 22—Feline GPR120 transient transfections in a stable cell line A.

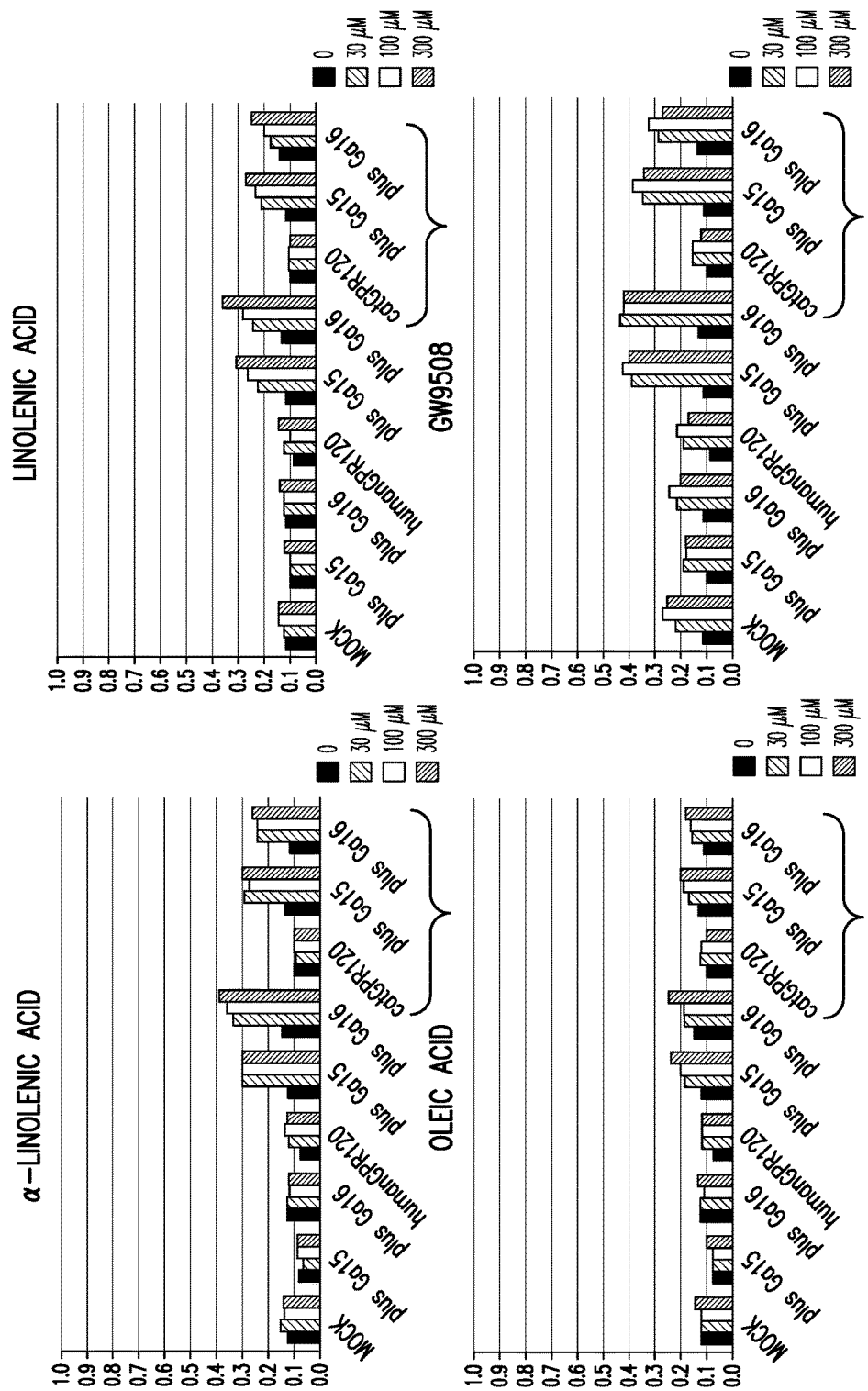
Figure 23 – Feline GPR120 transient transfections in CHOK1.

Figure 24 – Free fatty acid dose response curves and corresponding $EC_{50}$ values obtained using *in vitro* assay for cat GPR120.
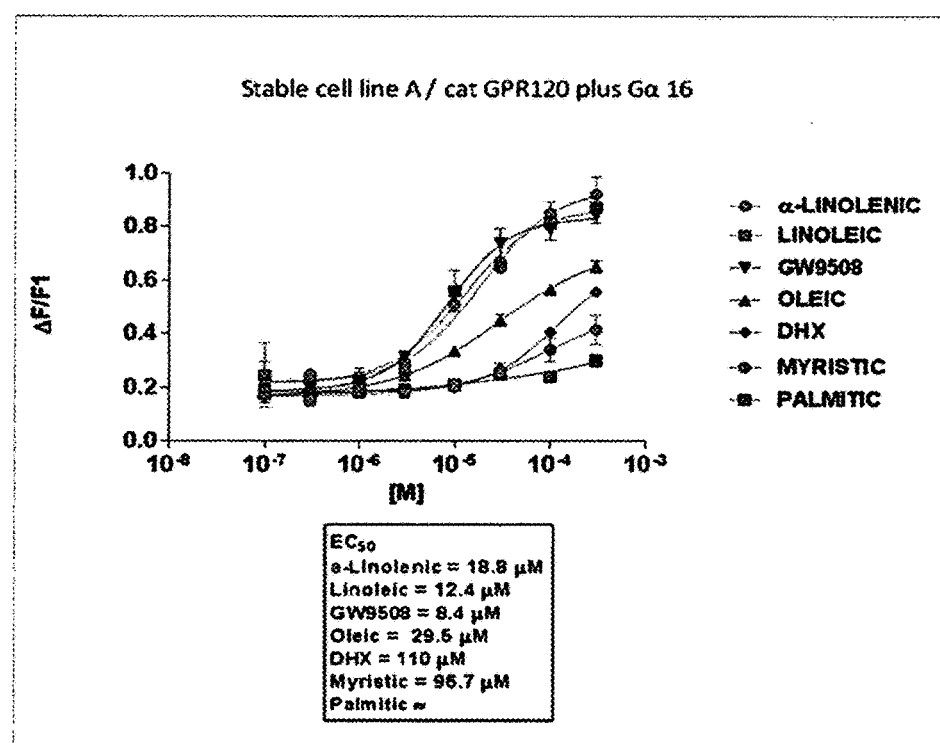

Figure 25 – Free fatty acid dose response curves and corresponding EC$_{50}$ values obtained using *in vitro* assay for cat GPR120 alone and with CD36 co-transfected.
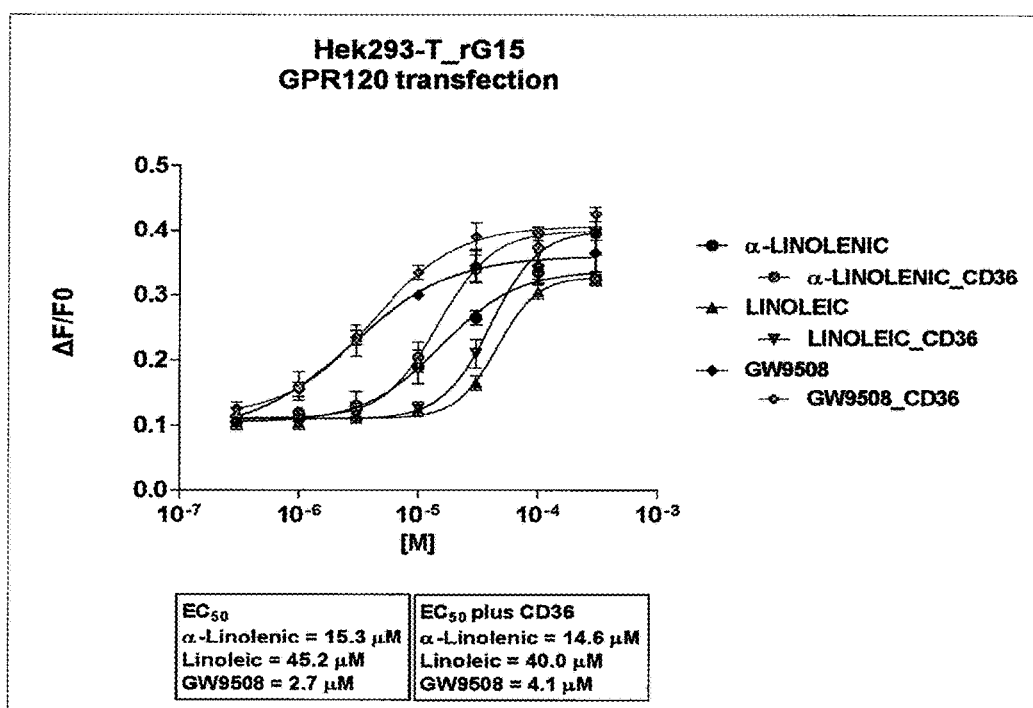

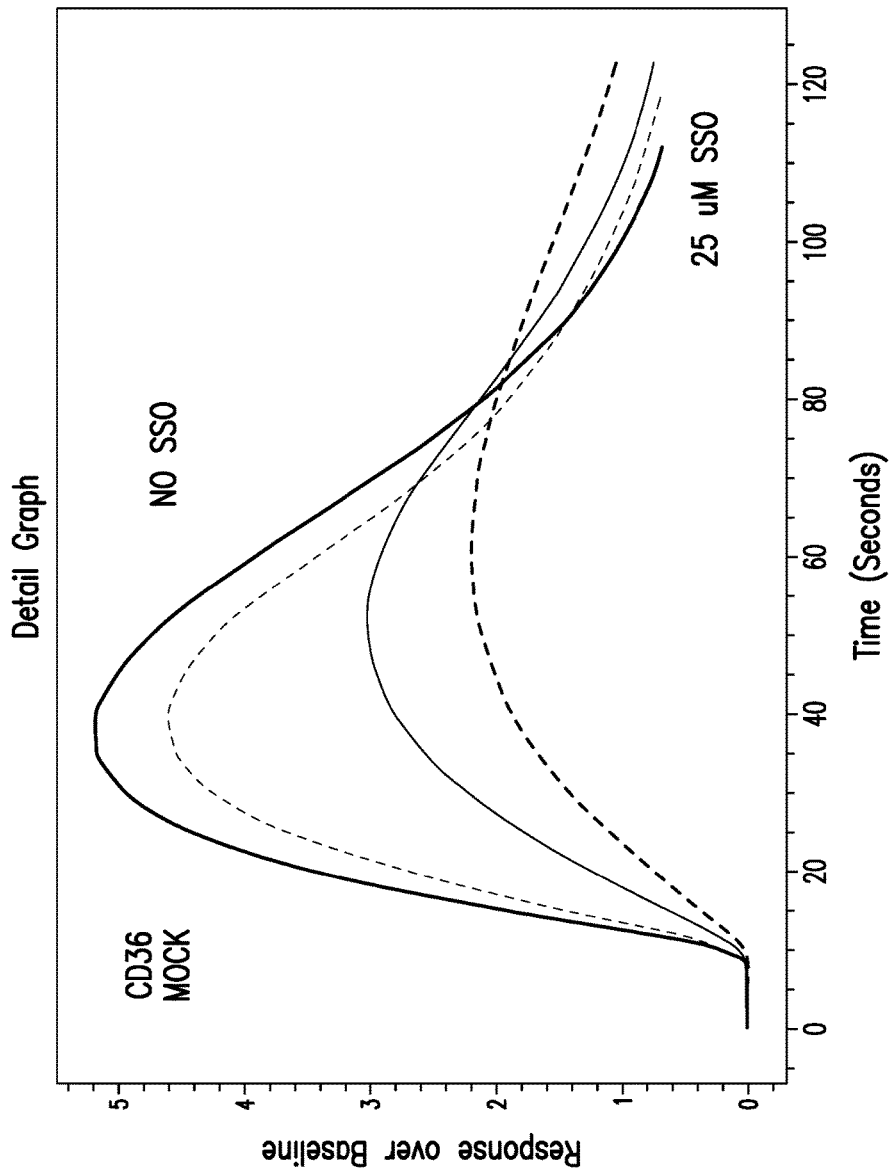
Figure 26–Fluorescence response for feline CD36 only in the presence of sulfo-N-succinimidyl oleate (SSO), which an antagonist of CD36.

Figure 27—Schematic of linoleic acid in the binding site of GPR120 using *in silico* modeling.
SIDE VIEW:
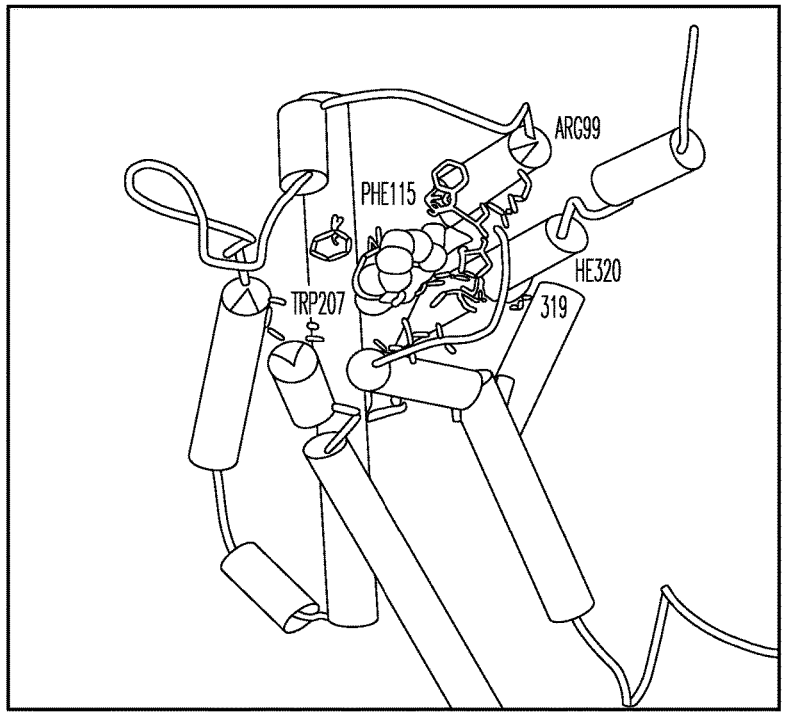
TOP VIEW:
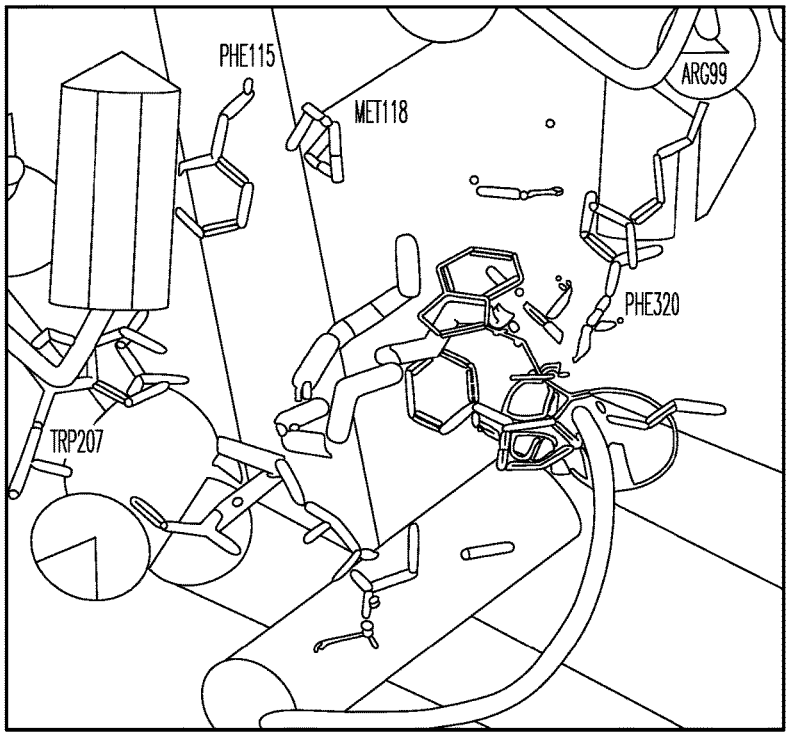

Figure 28—Schematic of oleic acid in the binding site of GPR120 using *in silico* modeling.
SIDE VIEW:
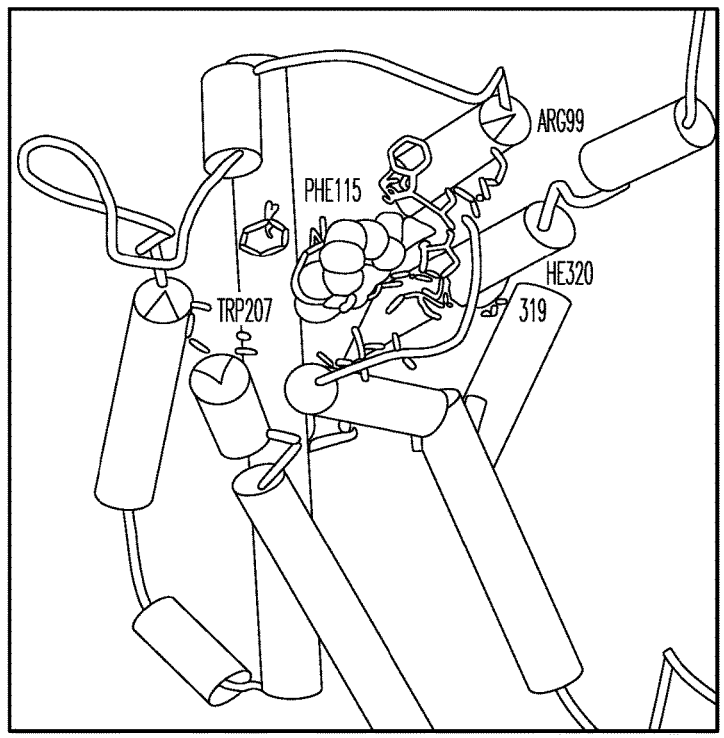
TOP VIEW:
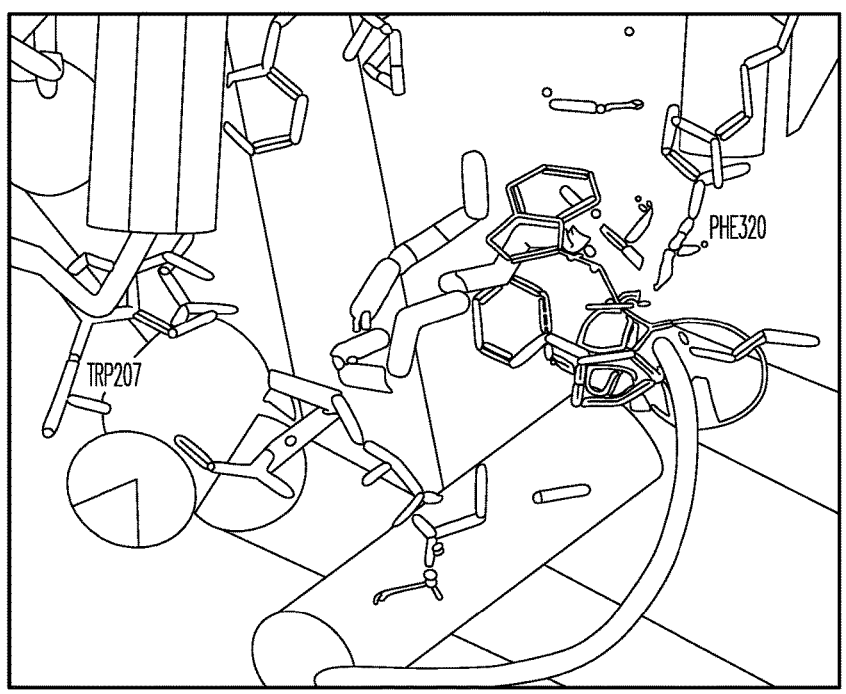

SEQUENCE LISTING

```
<160> NUMBER OF SEQ ID NOS: 12

<210> SEQ ID NO 1
<211> LENGTH: 361
<212> TYPE: PRT
<213> ORGANISM: Felis catus

<400> SEQUENCE: 1

Met Ser Pro Glu Cys Ala Gln Ala Ala Gly Thr Gly Ser Pro Arg Ser
1               5                   10                  15

Leu Glu Arg Ala Asn Arg Thr Arg Phe Pro Phe Phe Ser Asp Val Lys
            20                  25                  30

Gly Asp His Arg Leu Val Leu Thr Ala Val Glu Thr Val Val Leu Ala
        35                  40                  45

Leu Ile Phe Ala Val Ser Leu Leu Gly Asn Val Cys Ala Leu Val Leu
    50                  55                  60

Val Ala Arg Arg Arg Arg Gly Thr Thr Ala Cys Leu Val Leu Asn
65                  70                  75                  80

Leu Phe Cys Ala Asp Leu Leu Phe Thr Ser Ala Ile Pro Pro Val Leu
                85                  90                  95

Ala Val Arg Trp Thr Glu Ala Trp Leu Leu Gly Pro Val Ala Cys His
            100                 105                 110

Leu Leu Phe Tyr Val Met Ser Leu Ser Gly Ser Val Thr Ile Leu Thr
        115                 120                 125

Leu Ala Ala Val Ser Leu Glu Arg Met Val Cys Ile Val Arg Leu Gln
    130                 135                 140

Arg Gly Val Arg Gly Leu Gly Arg Arg Ala Arg Ala Ala Leu Leu Ala
145                 150                 155                 160

Leu Ile Trp Gly Tyr Ser Ala Leu Ala Ala Leu Pro Leu Cys Val Phe
                165                 170                 175
```

```
Phe Gln Val Val Pro Gln Arg Leu Ser Gly Arg Asp Gln Glu Ile Pro
            180                 185                 190
Ile Cys Thr Leu Ser Trp Pro Ser Ile Ala Gly Glu Ile Ser Trp Asp
        195                 200                 205
Val Ser Phe Val Thr Leu Asn Phe Leu Met Pro Gly Leu Leu Ile Val
    210                 215                 220
Ile Ser Tyr Ser Lys Ile Leu Gln Ile Thr Lys Ala Ser Arg Lys Arg
225                 230                 235                 240
Leu Thr Val Asn Leu Ala Ser Ser Glu Ser His His Ile Arg Val Ser
            245                 250                 255
Gln Gln Asp Phe Arg Leu Phe Arg Thr Leu Phe Leu Leu Met Ile Ser
            260                 265                 270
Phe Phe Ile Met Trp Ser Pro Ile Ile Ile Thr Ile Leu Leu Ile Leu
        275                 280                 285
Ile Gln Asn Phe Lys Gln Asp Leu Val Ile Trp Pro Ser Leu Phe Phe
        290                 295                 300
Trp Val Val Ala Phe Thr Phe Ala Asn Ser Ala Leu Asn Pro Ile Leu
305                 310                 315                 320
Tyr Asn Met Ser Leu Phe Arg Asn Glu Trp Arg Lys Ile Phe His Cys
            325                 330                 335
Phe Phe Tyr Pro Glu Lys Gly Ala Met Phe Thr Asp Thr Ser Val Arg
            340                 345                 350
Arg Asn Asp Leu Ser Val Ile Ser Asn
            355                 360

<210> SEQ ID NO 2
<211> LENGTH: 1086
<212> TYPE: DNA
<213> ORGANISM: Felis catus

<400> SEQUENCE: 2
atgtcccctg agtgcgcgca ggcggcgggc actgggtccc cgcgcagcct ggagcgggcc     60
aaccgcaccc gcttcccatt cttctccgac gtcaagggag accaccggct ggtgctgacc    120
gctgtggaga cggtcgtgct ggcgctcatc ttcgcggtgt cgctgttggg caacgtgtgc    180
gccttggtgc tggtggcgcg ccgacggcgc cgcggcacca ccgcctgcct ggtgctcaac    240
cttttctgcg cggacctgct cttcaccagc gccatcccgc ccgtgctggc tgtgcgatgg    300
actgaggcct ggctgctggg cccggtcgcc tgccacctgc tcttctacgt gatgagcttg    360
agcggcagcg tcaccatcct cacgctggcg ccgtcagcc tggagcgcat ggtgtgcatc    420
gttcgcctgc agcggggcgt gcggggcctg ggcggcggg cgagggccgc gctgctggcg    480
ctcatctggg gctactcggc gctggccgcg ctgcccctct gcgtcttctt ccaagtcgtt    540
ccgcagcggc tctccggtcg ggaccaggaa attccgattt gcacactgag ttggcccagc    600
atcgctggag aaatctcctg gatgtgtcg tttgttactt tgaactttt gatgccggga    660 ttgctcattg tgatcagcta ctccaagatt ttacagatca caaaggcatc aaggaaaagg    720
ctcacggtga acctggcttc ctcggagagc caccatatcc gcgtgtccca gcaggacttc    780
cggctcttcc gtaccctctt cctgctcatg atctccttct tcattatgtg gagccccatc    840
atcatcacca tcctcctcat cttgatccag aatttcaagc aggacctggt catctggcca    900
tccctcttct ctgggtggt ggccttcacg tttgccaact cagccctgaa ccccattctc    960
tataacatgt cactgtttag gaatgaatgg aggaaaattt tccattgctt cttctaccca   1020
```

```
gaaaagggag ccatgtttac agatacatct gtcagaagaa atgatctgtc cgttatttcc   1080
aactaa                                                              1086
```

<210> SEQ ID NO 3
<211> LENGTH: 472
<212> TYPE: PRT
<213> ORGANISM: Felis catus

<400> SEQUENCE: 3

```
Met Gly Cys Asp Arg Asn Cys Gly Leu Ile Ala Gly Ala Val Ile Gly
1               5                   10                  15

Ala Val Leu Ala Val Phe Gly Gly Ile Leu Met Pro Val Gly Asp Met
            20                  25                  30

Leu Ile Glu Arg Thr Ile Lys Lys Glu Val Val Leu Glu Glu Gly Thr
        35                  40                  45

Ile Ala Tyr Gln Asn Trp Val Lys Thr Gly Thr Glu Val Tyr Arg Gln
    50                  55                  60

Phe Trp Ile Tyr Asp Val Gln Asn Pro Gln Glu Val Val Ala Asn Ser
65                  70                  75                  80

Ser Lys Ile Lys Val Lys Gln Arg Gly Pro Tyr Thr Tyr Arg Val Arg
                85                  90                  95

Tyr Leu Ala Lys Lys Asn Ile Thr His Asp Pro Glu Thr His Thr Val
            100                 105                 110

Ser Phe Leu Gln Pro Asn Ala Ala Ile Phe Glu Pro Ser Leu Ser Ala
        115                 120                 125

Gly Thr Glu Asn Asp Thr Trp Thr Val Leu Asn Leu Ala Val Ala Ala
    130                 135                 140

Ala Pro His Leu Tyr Pro Asn Ala Phe Val Gln Val Val Leu Asn Ser
145                 150                 155                 160

Leu Ile Lys Lys Ser Lys Ser Met Phe Gln Lys Arg Thr Val Lys
                165                 170                 175

Glu Leu Leu Trp Gly Tyr Lys Asp Pro Phe Leu Ser Leu Val Pro Tyr
            180                 185                 190

Pro Ile Ser Thr Thr Val Gly Val Phe Phe Pro Tyr Asn Asn Thr Ala
        195                 200                 205

Asp Gly Val Tyr Thr Val Phe Ser Gly Lys Asp Asn Ile Ser Gln Val
    210                 215                 220

Ala Ile Ile Asp Thr Tyr Lys Gly Lys Lys Asn Leu Ser Tyr Trp Pro
225                 230                 235                 240

Ser Tyr Cys Asp Met Ile Asn Gly Thr Asp Ala Ala Ser Phe Pro Pro
                245                 250                 255

Phe Val Glu Lys Thr Arg Val Leu Arg Phe Phe Ser Ser Asp Ile Cys
            260                 265                 270

Arg Ser Ile Tyr Ala Val Phe Gly Ala Glu Ile Asn Leu Lys Gly Ile
        275                 280                 285

Pro Val Tyr Arg Phe Val Leu Pro Ser Met Ala Phe Ala Ser Pro Leu
    290                 295                 300

Gln Asn Pro Asp Asn His Cys Phe Cys Thr Glu Thr Val Ile Ser Asn
305                 310                 315                 320

Asn Cys Thr Ser Tyr Gly Val Leu Asp Ile Gly Arg Cys Lys Glu Gly
                325                 330                 335

Lys Pro Val Tyr Ile Ser Leu Pro His Phe Leu His Ala Ser Pro Asp
            340                 345                 350

Ile Ala Glu Pro Ile Glu Gly Leu Thr Pro Asn Glu Asp Glu His Ser
```

```
                355                 360                 365
Thr Tyr Leu Asp Val Glu Pro Ile Thr Gly Phe Thr Leu Arg Phe Ala
    370                 375                 380

Lys Arg Leu Gln Ile Asn Ile Leu Val Lys Pro Ala Lys Lys Ile Glu
385                 390                 395                 400

Ala Leu Lys Gly Leu Lys Arg Asn Tyr Ile Val Pro Ile Leu Trp Leu
                405                 410                 415

Asn Glu Thr Gly Thr Ile Gly Asp Glu Lys Ala Glu Met Phe Arg Lys
            420                 425                 430

Arg Val Thr Gly Lys Ile Asn Leu Leu Gly Leu Val Glu Ile Thr Leu
                435                 440                 445

Leu Ser Val Gly Val Val Met Phe Val Ala Phe Met Ile Ser Tyr Cys
        450                 455                 460

Ala Cys Arg Ser Lys Lys Val Lys
465                 470

<210> SEQ ID NO 4
<211> LENGTH: 1419
<212> TYPE: DNA
<213> ORGANISM: Felis catus

<400> SEQUENCE: 4
atgggctgtg accgaaactg tgggctcatt gctggtgctg tcattggtgc agtcctggcc    60
gtgtttggag gcattctaat gccagtcgga gacatgctta ttgagaggac aatcaaaaag   120
gaggttgtac tcgaggaagg taccattgct atcaaaatt gggttaaaac aggcacagaa    180
gtttacagac agttttggat ctatgatgtg caaaacccac aggaagtggt agctaatagc   240
agcaaaatta agttaaaca aagaggtcct tacacgtaca gagttcgtta tctagccaaa    300
aaaaatataa cccacgatcc tgagacccac acagtctctt tcttcagcc caatgcggcc    360 atcttcgagc cttcactatc agctggaaca gagaatgaca cttggactgt tctcaatctg   420
gctgtagcag ctgcacccca tctctaccca aatgcatttg ttcaagtggt actcaattca   480
cttatcaaaa agtcaaaatc ttccatgttt caaaaaagaa ctgtgaaaga gctcttgtgg   540
ggctataaag atccgttctt gagtttggtt ccatatccta tttccacgac agttggtgtg   600
tttttttcct tacaacaac tgcagatgga gtttatacag ttttcagtgg gaaagacaac    660
atcagccaag ttgccataat tgacacttac aaaggtaaaa gaatctctc ctattggcca    720 agttattgtg acatgattaa tggtacagac gcagcctcat tccacctttt gttgagaag    780 acgcgagtgt tacgttttctt ttcttctgac atttgcaggt caatctatgc tgtgtttgga   840
gctgaaatta acctgaaagg aatccctgtc tatagatttg ttcttccatc catggccttt    900
gcatctccac ttcaaaatcc agataaccat tgtttctgca cagaaaccgt tatctccaat    960
aattgtacat catatggtgt attagacatt ggcagatgca agaaggaaaa acctgtgtat   1020
atttcacttc ctcattttct acatgcaagt cctgatattg cagaacccat tgaaggctta   1080
actccaaatg aagacgaaca tagcacatac ttagatgttg aacctataac tggattcact   1140
ttacgatttg caaacggct gcaaatcaac atattggtca aaccagcaaa gaaaattgag   1200
gcattaaagg gtcttaagcg gaactatatt gtgcctattc tttggcttaa tgagactggt   1260
accattggtg atgagaaggc agaaatgttt agaaaaagag tgactggaaa aatcaacctt   1320
cttggcctgg tagaaattac cttactcagt gttggcgtgg tgatgtttgt tgctttatg   1380 atttcatact gtgcgtgcag atcaaagaaa gtaaaataa                         1419
```

<210> SEQ ID NO 5
<211> LENGTH: 361
<212> TYPE: PRT
<213> ORGANISM: Canis familiaris

<400> SEQUENCE: 5

```
Met Ser Pro Glu Cys Ala Gln Ala Pro Gly Ala Gly Ser Pro Arg Ser
1               5                   10                  15

Leu Glu Arg Ala Asn Arg Thr Arg Phe Pro Phe Phe Ser Asp Val Lys
                20                  25                  30

Gly Asp His Arg Leu Val Leu Thr Ala Val Glu Thr Val Leu Ala
                35                  40                  45

Leu Ile Phe Ala Val Ser Leu Leu Gly Asn Val Cys Ala Leu Val Leu
        50                  55                  60

Val Ala Arg Arg Arg Arg Gly Thr Thr Ala Cys Leu Val Leu Asn
65                  70                  75                  80

Leu Phe Cys Ala Asp Leu Leu Phe Thr Ser Ala Ile Pro Pro Val Leu
                85                  90                  95

Ala Val Arg Trp Thr Glu Ala Trp Leu Leu Gly Pro Val Ala Cys His
                100                 105                 110

Leu Leu Phe Tyr Val Met Ser Leu Ser Gly Ser Val Thr Ile Leu Thr
            115                 120                 125

Leu Ala Ala Val Ser Leu Glu Arg Val Val Cys Ile Val Arg Leu Gln
        130                 135                 140

Arg Gly Ala Arg Gly Leu Gly Arg Arg Ala Arg Ala Ala Leu Leu Ala
145                 150                 155                 160

Leu Val Trp Gly Tyr Ser Ala Leu Ala Ala Leu Pro Leu Cys Val Phe
                165                 170                 175

Phe His Val Val Pro Gln Arg Leu Pro Gly Arg Asp Gln Glu Ile Leu
                180                 185                 190

Ile Cys Thr Leu Ala Trp Thr Ser Val Ala Gly Glu Ile Ser Trp Asp
            195                 200                 205

Val Ser Phe Val Thr Leu Asn Phe Leu Val Pro Gly Leu Leu Ile Val
        210                 215                 220

Ile Ser Tyr Ser Lys Ile Leu Gln Ile Thr Lys Ala Ser Arg Lys Arg
225                 230                 235                 240

Leu Thr Val Asn Leu Ala Tyr Ser Glu Ser His His Ile Arg Val Ser
                245                 250                 255

Gln Gln Asp Phe Arg Leu Phe Arg Thr Leu Phe Leu Leu Met Ile Ser
                260                 265                 270

Phe Phe Ile Met Trp Ser Pro Ile Ile Ile Thr Ile Leu Leu Ile Leu
            275                 280                 285

Ile Gln Asn Phe Lys Gln Asp Leu Val Ile Trp Pro Ser Leu Phe Phe
        290                 295                 300

Trp Val Val Ala Phe Thr Phe Ala Asn Ser Ala Leu Asn Pro Ile Leu
305                 310                 315                 320

Tyr Asn Met Ser Leu Phe Arg Asn Glu Trp Arg Lys Ile Phe His Cys
                325                 330                 335

Phe Phe Tyr Pro Glu Lys Gly Ala Met Phe Thr Asp Thr Ser Val Arg
                340                 345                 350

Arg Asn Asp Leu Ser Ile Ile Tyr Ser
        355                 360
```

<210> SEQ ID NO 6

```
<211> LENGTH: 1086
<212> TYPE: DNA
<213> ORGANISM: Canis familiaris

<400> SEQUENCE: 6
atgtcccctg agtgcgcgca ggcgccgggc gccgggtccc cgcgcagcct ggagcgggcc      60
aaccgcaccc gcttcccctt cttctccgac gtcaagggcg accaccggct ggtgctgacc     120
gccgtggaga cggtcgtgct ggcgctcatc ttcgcggtgt cgctgttggg caacgtgtgc     180
gccttggtgc tggtggcgcg ccgacggcgc cgcggcacca ccgcctgcct ggtgctcaac     240
ctcttctgcg ccgacctgct cttcaccagc gccatcccgc ccgtgctggc cgtgcggtgg     300
accgaggcct ggctgctggg cccggtcgcc tgccacctgc tcttctacgt gatgagcctg     360
agcggcagcg tcaccatcct cacgctggcg gccgtcagcc tggagcgcgt ggtgtgcatc     420
gtccgcctgc agcggggcgc gcggggcctg gggcggcggg cgagggccgc gctgctggcg     480
ctcgtctggg gctactcggc gctcgccgcg ctgccgctct gcgtcttctt ccacgtcgtc     540
ccccagcggc tgcccggtcg cgaccaggaa attctgattt gcacactggc ttggaccagt     600
gttgccggag aaatctcctg ggacgtgtcg tttgttactt tgaacttctt ggtaccagga     660

ttgctcattg tgatcagcta ctccaaaatt ttacagatca caaaggcgtc aaggaaaagg     720
ctcacggtga acctagctta ctcagagagc caccatatcc gcgtgtccca gcaggacttc     780
cggctcttcc gcacgctctt cctgctcatg atctccttct tcattatgtg gagccccatc     840
atcatcacca tcctcctcat cttgatccag aacttcaagc aagacttggt catctggcca     900

tccctcttct tctgggtggt ggcattcacg tttgccaact cggccccтgaa ccccattctc     960

tataacatgt cactgtttag gaatgaatgg aggaaaattt ttcactgctt cttctaccca    1020
gaaaagggag ccatgtttac agatacatct gtcagaagaa atgatctgtc aattatttac    1080
agctaa                                                              1086

<210> SEQ ID NO 7
<211> LENGTH: 472
<212> TYPE: PRT
<213> ORGANISM: Canis familiaris

<400> SEQUENCE: 7

Met Gly Cys Asp Arg Asn Cys Gly Leu Ile Ala Gly Ala Val Ile Gly
1               5                   10                  15

Ala Val Leu Ala Leu Leu Gly Gly Ile Leu Met Pro Val Gly Asp Met
            20                  25                  30

Leu Ile Glu Lys Thr Ile Lys Lys Glu Val Val Leu Glu Gly Thr
        35                  40                  45

Ile Ala Phe Lys Asn Trp Val Lys Thr Gly Thr Glu Val Tyr Arg Gln
    50                  55                  60

Phe Trp Ile Phe Asp Val Gln Asn Ala Gln Glu Val Val Ala Asn Ser
65                  70                  75                  80

Ser Lys Ile Lys Val Lys Gln Arg Gly Pro Tyr Thr Tyr Arg Val Arg
                85                  90                  95

Tyr Leu Ala Lys Glu Asn Ile Thr His Asp Thr Glu Asn His Leu Val
            100                 105                 110

Ser Phe Val Gln Pro Asn Gly Ala Ile Phe Glu Pro Ser Leu Ser Val
        115                 120                 125

Gly Thr Glu Asp Asp Thr Met Thr Val Leu Asn Leu Ala Val Ala Ala
    130                 135                 140
```

```
Ala Pro His Leu Tyr Pro Asn Ala Phe Val Gln Val Val Leu Asn Ser
145                 150                 155                 160

Leu Ile Lys Lys Ser Lys Ser Ser Met Phe Gln Asn Arg Thr Val Lys
                165                 170                 175

Glu Leu Leu Trp Gly Tyr Thr Asp Pro Phe Leu Ser Leu Val Pro Tyr
            180                 185                 190

Pro Val Asn Thr Lys Val Gly Val Phe Tyr Pro Tyr Asn Asn Thr Val
        195                 200                 205

Asp Gly Val Tyr Ser Val Phe Ser Gly Lys Asp Asn Val Ser Gln Val
    210                 215                 220

Ala Ile Ile Asp Thr Tyr Lys Gly Lys Asn Leu Ser Tyr Trp Pro
225                 230                 235                 240

Ser Tyr Cys Asp Met Ile Asn Gly Thr Asp Ala Ala Ser Phe Pro Pro
                245                 250                 255

Phe Val Glu Lys Thr Arg Val Leu Arg Phe Phe Ser Ser Asp Ile Cys
            260                 265                 270

Arg Ser Ile Tyr Ala Val Phe Gly Ala Glu Ile Asn Leu Lys Gly Ile
        275                 280                 285

Pro Val Tyr Arg Phe Val Leu Pro Ser Met Ala Phe Ala Ser Pro Leu
    290                 295                 300

Gln Asn Pro Asp Asn His Cys Phe Cys Thr Glu Lys Val Ile Ser Asn
305                 310                 315                 320

Asn Cys Thr Ser Tyr Gly Val Leu Asp Ile Gly Lys Cys Lys Glu Gly
                325                 330                 335

Lys Pro Val Tyr Ile Ser Leu Pro His Phe Leu His Ala Ser Pro Asp
            340                 345                 350

Ile Gly Glu Pro Ile Glu Gly Leu Ser Pro Asn Glu Asp Glu His Thr
        355                 360                 365

Thr Tyr Leu Asp Val Glu Pro Ile Thr Gly Phe Thr Leu Arg Phe Ala
    370                 375                 380

Lys Arg Leu Gln Ile Asn Ile Leu Val Lys Pro Ala Lys Lys Ile Glu
385                 390                 395                 400

Ala Leu Lys Asn Leu Lys Arg Asn Tyr Ile Val Pro Ile Leu Trp Leu
                405                 410                 415

Asn Glu Thr Gly Thr Ile Gly Asp Glu Lys Ala Ala Gln Phe Arg Lys
            420                 425                 430

Gln Val Thr Gly Lys Ile Asn Leu Leu Gly Leu Val Glu Ile Ile Leu
        435                 440                 445

Leu Thr Val Gly Val Val Met Phe Val Ala Phe Met Ile Ser Tyr Cys
    450                 455                 460

Ala Cys Arg Ser Lys Gly Lys Arg
465                 470

<210> SEQ ID NO 8
<211> LENGTH: 1419
<212> TYPE: DNA
<213> ORGANISM: Canis familiaris

<400> SEQUENCE: 8
atgggctgtg accgcaactg tgggctcatc gcgggcgctg tcatcggggc agtgctcgcc      60
ctgctggggg gcattctgat gcccgtcgga gacatgctga ttgagaagac aatcaagaag     120
gaagttgtac ttgaagaagg tacaattgct ttcaaaaatt gggttaaaac aggcacagaa     180
gtttacagac agtttggat ctttgacgtg caaaatgcac aggaagtggt tgcgaacagc     240
```

```
agcaaaatta aggttaaaca aagaggtcct tacacataca gagttcgtta tctagccaaa    300
gaaaatataa ctcatgacac tgagaaccac ttagtctctt ttgtccagcc caacggtgcc    360
atctttgaac cttcactatc tgttggaaca gaagatgaca ctatgaccgt tctcaatctg    420
gctgtagcag ctgcacccca tctctatcca aatgcatttg ttcaagtggt actcaattca    480
cttatcaaaa agtcaaaatc gtctatgttt caaaatagaa ctgtgaaaga gctcttgtgg    540
ggctacacgg atccattctt gagtttggtt ccatacctg ttaacacaaa agttggtgtg     600
ttttatcctt acaacaacac tgtcgatgga gtttattcag ttttcagtgg aaagacaac    660 gtaagccaag ttgccataat tgacacttac aaaggtaaaa agaatctctc ctattggcca    720
agttattgtg acatgattaa tggtacagat gcagcctcat ttccaccttt tgtagagaag    780
acacgagtat tgcgtttctt ttcctctgac atttgcaggt caatctatgc tgtgtttgga    840
gctgaaatta acctgaaagg aattcctgtc tatagatttg ttcttccatc catggccttt    900
gcatctccac ttcaaaatcc agataatcat tgtttctgca cagaaaaagt tatctcaaat    960
aactgcacat catatggtgt gctagacatt ggcaaatgca agaaggaaa acctgtgtat    1020 atttcacttc ctcatttct acatgcaagt cctgatattg agaacctat tgaaggctta    1080 agtccaaatg aagatgaaca taccacatac ttagatgttg aacctataac tggattcact    1140
ttacgatttg caaacggct gcaaatcaac atattggtca agccagcaaa aaaaattgaa    1200
gcattaaaga atctgaagcg aaactacatt gtacctattc tttggcttaa tgagactggt    1260
accatcggtg atgagaaggc agcacagttc agaaaacaag tgaccggaaa aataaacctc    1320
cttggcctgg tagaaatcat cttactcact gttggtgtgg tgatgtttgt tgcttttatg    1380
atttcatact gtgcatgcag atcaaaggga aaaagataa                          1419
```

<210> SEQ ID NO 9
<211> LENGTH: 361
<212> TYPE: PRT
<213> ORGANISM: Homo sapiens

<400> SEQUENCE: 9

```
Met Ser Pro Glu Cys Ala Arg Ala Ala Gly Asp Ala Pro Leu Arg Ser
1               5                   10                  15

Leu Glu Gln Ala Asn Arg Thr Arg Phe Pro Phe Phe Ser Asp Val Lys
            20                  25                  30

Gly Asp His Arg Leu Val Leu Ala Val Glu Thr Thr Val Leu Val
        35                  40                  45

Leu Ile Phe Ala Val Ser Leu Leu Gly Asn Val Cys Ala Leu Val Leu
    50                  55                  60

Val Ala Arg Arg Arg Arg Gly Ala Thr Ala Cys Leu Val Leu Asn
65                  70                  75                  80

Leu Phe Cys Ala Asp Leu Leu Phe Ile Ser Ala Ile Pro Leu Val Leu
                85                  90                  95

Ala Val Arg Trp Thr Glu Ala Trp Leu Leu Gly Pro Val Ala Cys His
            100                 105                 110

Leu Leu Phe Tyr Val Met Thr Leu Ser Gly Ser Val Thr Ile Leu Thr
        115                 120                 125

Leu Ala Ala Val Ser Leu Glu Arg Met Val Cys Ile Val His Leu Gln
    130                 135                 140

Arg Gly Val Arg Gly Pro Gly Arg Arg Ala Arg Ala Val Leu Leu Ala
145                 150                 155                 160

Leu Ile Trp Gly Tyr Ser Ala Val Ala Ala Leu Pro Leu Cys Val Phe
```

```
              165                 170                 175
Phe Arg Val Val Pro Gln Arg Leu Pro Gly Ala Asp Gln Glu Ile Ser
            180                 185                 190

Ile Cys Thr Leu Ile Trp Pro Thr Ile Pro Gly Glu Ile Ser Trp Asp
            195                 200                 205

Val Ser Phe Val Thr Leu Asn Phe Leu Val Pro Gly Leu Val Ile Val
        210                 215                 220

Ile Ser Tyr Ser Lys Ile Leu Gln Ile Thr Lys Ala Ser Arg Lys Arg
225                 230                 235                 240

Leu Thr Val Ser Leu Ala Tyr Ser Glu Ser His Gln Ile Arg Val Ser
                245                 250                 255

Gln Gln Asp Phe Arg Leu Phe Arg Thr Leu Phe Leu Leu Met Val Ser
            260                 265                 270

Phe Phe Ile Met Trp Ser Pro Ile Ile Thr Ile Leu Leu Ile Leu
            275                 280                 285

Ile Gln Asn Phe Lys Gln Asp Leu Val Ile Trp Pro Ser Leu Phe Phe
        290                 295                 300

Trp Val Val Ala Phe Thr Phe Ala Asn Ser Ala Leu Asn Pro Ile Leu
305                 310                 315                 320

Tyr Asn Met Thr Leu Cys Arg Asn Glu Trp Lys Lys Ile Phe Cys Cys
                325                 330                 335

Phe Trp Phe Pro Glu Lys Gly Ala Ile Leu Thr Asp Thr Ser Val Lys
            340                 345                 350

Arg Asn Asp Leu Ser Ile Ile Ser Gly
            355                 360

<210> SEQ ID NO 10
<211> LENGTH: 1086
<212> TYPE: DNA
<213> ORGANISM: Homo sapiens

<400> SEQUENCE: 10
atgtcccctg aatgcgcgcg ggcagcgggc gacgcgccct tgcgcagcct ggagcaagcc      60
aaccgcaccc gctttccctt cttctccgac gtcaagggcg accaccggct ggtgctggcc     120
gcggtggaga caaccgtgct ggtgctcatc tttgcagtgt cgctgctggg caacgtgtgc     180
gccctggtgc tggtggcgcg ccgacgacgc gcggcgcga ctgcctgcct ggtactcaac     240
ctcttctgcg cggacctgct cttcatcagc gctatccctc tggtgctggc cgtgcgctgg     300
actgaggcct ggctgctggg ccccgttgcc tgccacctgc tcttctacgt gatgaccctg     360
agcggcagcg tcaccatcct cacgctggcc gcggtcagcc tggagcgcat ggtgtgcatc     420
gtgcacctgc agcgcggcgt gcggggtcct gggcggcggg cgcgggcagt gctgctggcg     480
ctcatctggg gctattcggc ggtcgccgct ctgcctctct gcgtcttctt ccgagtcgtc     540
ccgcaacggc tccccggcgc cgaccaggaa atttcgattt gcacactgat ttggcccacc     600
attcctggag agatctcgtg ggatgtctct tttgttactt tgaacttctt ggtgccagga     660
ctggtcattg tgatcagtta ctccaaaatt ttacagatca caaaggcatc aaggaagagg     720
ctcacggtaa gctggccta ctcggagagc accagatcc gcgtgtccca gcaggacttc     780
cggctcttcc gcaccctctt cctcctcatg gtctccttct tcatcatgtg gagccccatc     840
atcatcacca tcctcctcat cctgatccag aacttcaagc aagacctggt catctggccg     900
tccctcttct tctgggtggt ggccttcaca tttgctaatt cagccctaaa ccccatcctc     960
tacaacatga cactgtgcag gaatgagtgg aagaaaattt tttgctgctt ctggttccca    1020
```

```
gaaaagggag ccattttaac agacacatct gtcaaaagaa atgacttgtc gattatttct    1080
ggctaa                                                                1086
```

<210> SEQ ID NO 11
<211> LENGTH: 472
<212> TYPE: PRT
<213> ORGANISM: Homo sapiens

<400> SEQUENCE: 11

```
Met Gly Cys Asp Arg Asn Cys Gly Leu Ile Ala Gly Ala Val Ile Gly
1               5                   10                  15

Ala Val Leu Ala Val Phe Gly Gly Ile Leu Met Pro Val Gly Asp Leu
                20                  25                  30

Leu Ile Gln Lys Thr Ile Lys Lys Gln Val Val Leu Glu Glu Gly Thr
            35                  40                  45

Ile Ala Phe Lys Asn Trp Val Lys Thr Gly Thr Glu Val Tyr Arg Gln
        50                  55                  60

Phe Trp Ile Phe Asp Val Gln Asn Pro Gln Glu Val Met Met Asn Ser
65                  70                  75                  80

Ser Asn Ile Gln Val Lys Gln Arg Gly Pro Tyr Thr Tyr Arg Val Arg
                85                  90                  95

Phe Leu Ala Lys Glu Asn Val Thr Gln Asp Ala Glu Asp Asn Thr Val
            100                 105                 110

Ser Phe Leu Gln Pro Asn Gly Ala Ile Phe Glu Pro Ser Leu Ser Val
        115                 120                 125

Gly Thr Glu Ala Asp Asn Phe Thr Val Leu Asn Leu Ala Val Ala Ala
130                 135                 140

Ala Ser His Ile Tyr Gln Asn Gln Phe Val Gln Met Ile Leu Asn Ser
145                 150                 155                 160

Leu Ile Asn Lys Ser Lys Ser Ser Met Phe Gln Val Arg Thr Leu Arg
                165                 170                 175

Glu Leu Leu Trp Gly Tyr Arg Asp Pro Phe Leu Ser Leu Val Pro Tyr
            180                 185                 190

Pro Val Thr Thr Thr Val Gly Leu Phe Tyr Pro Tyr Asn Asn Thr Ala
        195                 200                 205

Asp Gly Val Tyr Lys Val Phe Asn Gly Lys Asp Asn Ile Ser Lys Val
210                 215                 220

Ala Ile Ile Asp Thr Tyr Lys Gly Lys Arg Asn Leu Ser Tyr Trp Glu
225                 230                 235                 240

Ser His Cys Asp Met Ile Asn Gly Thr Asp Ala Ala Ser Phe Pro Pro
                245                 250                 255

Phe Val Glu Lys Ser Gln Val Leu Gln Phe Phe Ser Ser Asp Ile Cys
            260                 265                 270

Arg Ser Ile Tyr Ala Val Phe Glu Ser Asp Val Asn Leu Lys Gly Ile
        275                 280                 285

Pro Val Tyr Arg Phe Val Leu Pro Ser Lys Ala Phe Ala Ser Pro Val
        290                 295                 300

Glu Asn Pro Asp Asn Tyr Cys Phe Cys Thr Glu Lys Ile Ile Ser Lys
305                 310                 315                 320

Asn Cys Thr Ser Tyr Gly Val Leu Asp Ile Ser Lys Cys Lys Glu Gly
                325                 330                 335

Arg Pro Val Tyr Ile Ser Leu Pro His Phe Leu Tyr Ala Ser Pro Asp
            340                 345                 350
```

```
Val Ser Glu Pro Ile Asp Gly Leu Asn Pro Asn Glu Glu His Arg
        355                 360                 365

Thr Tyr Leu Asp Ile Glu Pro Ile Thr Gly Phe Thr Leu Gln Phe Ala
    370                 375                 380

Lys Arg Leu Gln Val Asn Leu Leu Val Lys Pro Ser Glu Lys Ile Gln
385                 390                 395                 400

Val Leu Lys Asn Leu Lys Arg Asn Tyr Ile Val Pro Ile Leu Trp Leu
                405                 410                 415

Asn Glu Thr Gly Thr Ile Gly Asp Glu Lys Ala Asn Met Phe Arg Ser
            420                 425                 430

Gln Val Thr Gly Lys Ile Asn Leu Leu Gly Leu Ile Glu Met Ile Leu
        435                 440                 445

Leu Ser Val Gly Val Val Met Phe Val Ala Phe Met Ile Ser Tyr Cys
    450                 455                 460

Ala Cys Arg Ser Lys Thr Ile Lys
465                 470

<210> SEQ ID NO 12
<211> LENGTH: 1419
<212> TYPE: DNA
<213> ORGANISM: Homo sapiens

<400> SEQUENCE: 12
atgggctgtg accggaactg tgggctcatc gctggggctg tcattggtgc tgtcctggct      60
gtgtttggag gtattctaat gccagttgga gacctgctta ccagaagac aattaaaaag     120 caagttgtcc tcgaagaagg tacaattgct tttaaaaatt gggttaaaac aggcacagaa     180
gtttacagac agttttggat ctttgatgtg caaaatccac aggaagtgat gatgaacagc     240
agcaacattc aagttaagca aagaggtcct tatacgtaca gagttcgttt tctagccaag     300
gaaaatgtaa cccaggacgc tgaggacaac acagtctctt cctgcagcc caatggtgcc     360 atcttcgaac cttcactatc agttggaaca gaggctgaca acttcacagt tctcaatctg     420
gctgtggcag ctgcatccca tatctatcaa aatcaatttg ttcaaatgat cctcaattca     480
cttattaaca gtcaaaatc ttctatgttc aagtcagaa ctttgagaga actgttatgg     540
ggctataggg atccattttt gagtttggtt ccgtaccctg ttactaccac agttggtctg     600
ttttatcctt acaacaatac tgcagatgga gtttataaag ttttcaatgg aaaagataac     660
ataagtaaag ttgccataat cgacacatat aaaggtaaaa ggaatctgtc ctattgggaa     720
agtcactgcg acatgattaa tggtacagat gcagcctcat tccacccttt tgttgagaaa     780
agccaggtat tgcagttctt ttcttctgat atttgcaggt caatctatgc tgtatttgaa     840
tccgacgtta atctgaaagg aatccctgtg tatagatttg ttcttccatc caaggccttt     900
gcctctccag ttgaaaaccc agacaactat tgtttctgca cagaaaaaat tatctcaaaa     960
aattgtacat catatggtgt gctagacatc agcaaatgca agaagggag acctgtgtac    1020 atttcacttc ctcatttct gtatgcaagt cctgatgttt cagaacctat tgatggatta    1080
aacccaaatg aagaagaaca taggacatac ttggatattg aacctataac tggattcact    1140
ttacaatttg caaacggct gcaggtcaac ctattggtca agccatcaga aaaaattcaa    1200
gtattaaaga atctgaagag gaactatatt gtgcctattc tttggcttaa tgagactggg    1260
```

```
accattggtg atgagaaggc aaacatgttc agaagtcaag taactggaaa aataaacctc    1320
cttggcctga tagaaatgat cttactcagt gttggtgtgg tgatgtttgt tgcttttatg    1380
atttcatatt gtgcatgcag atcgaaaaca ataaaataa                            1419
```

METHODS FOR INCREASING PALATABILITY OF PET FOODSTUFF

CROSS-REFERENCE TO RELATED APPLICATIONS

This application is a divisional of U.S. patent application Ser. No. 14/898,321, filed Dec. 14, 2015, which is a U.S. National Stage Patent Application under 35 U.S.C. § 371 of and claims priority to International Application No. PCT/GB2014/000233, filed Jun. 13, 2014, which claims priority to GB Patent Application No. 1310664.6, filed Jun. 14, 2013, the contents of each of which are hereby incorporated by reference in their entireties, and to which priority is claimed.

SEQUENCE LISTING

The instant application contains a Sequence Listing which has been submitted electronically in ASCII format and is hereby incorporated by reference in its entirety. Pursuant to 37 C.F.R. § 1.52(e)(5), the Sequence Listing text file, identified as 069269_0295_Sequence_Listing.txt, is 32,505 bytes and was created on Dec. 19, 2018. The Sequence Listing, electronically filed herewith, does not extend beyond the scope of the specification and thus does not contain new matter.

FIELD

The present invention relates to a method of identifying a compound that binds to or modulates the activity of one or more polypeptides encoding one or more receptors that are involved in the detection and perception of fatty acids.

BACKGROUND OF THE INVENTION

It is well known that many feline and canine companion animals are fussy with their food. An animal will often refuse to eat a foodstuff that it has been eating for some time, or refuse to eat any more than a minimal amount of a foodstuff. Part of this phenomenon can be driven by subtle differences in the sensory profile of the raw materials. These differences might not be perceived by the human consumer, but due to differences in the olfactory and gustatory systems, feline and canine companion animals may well perceive these differences. These sensory differences can be due to natural variation of the raw materials used or when materials are in short supply and have to be substituted with alternatives. This can be very frustrating for the owner and can result in the owner perceiving that the animal is unhappy and not enjoying its food. An animal may also fail to ingest its required amount of essential nutrients if not consuming an adequate amount of food available to it. Therefore, it can clearly be seen that there exists a need for a way to encourage companion animals to eat the foodstuff with which it is provided. Many solutions have been suggested to overcome this problem. Most commercially available pet foods are provided in a range of different flavours and/or textures. However, the companion animal owner will know that often a companion animal will suddenly, for no clear reason, refuse the flavour that the owner perceives to be its most preferred. Much research has been carried out on the flavour preferences of companion animals, by offering them a choice of different foodstuffs.

Taste perception in mammalian animals is governed by the taste receptors found on taste buds of the tongue of the animal and has generally been considered to involve five taste perceptions; salt, sweet, bitter, sour and umami. The taste of a food is determined by which receptors are stimulated. Although some taste receptors share homology between species, the prevalence, frequency and activity of each receptor type depends on the species, since, as would be expected, an herbivorous animal will require different taste stimuli than a carnivorous animal. Feline and canine taste receptors share some homology with those of human, although, as is known, different receptors have different levels of activation and/or preference in feline and canine animals than in humans.

The perception of fat in foods is generally thought to have been due to mouth feel and, to some extent, smell. However, in the human and rodent fields, fatty acid taste receptors have recently been identified (Cartoni et al, 2010; Galindo et al 2012; Martin et al, 2011), indicating that a taste response is also involved in fat perception and detection.

GPR120 (also known as GPR129, O3FAR1, PGR4, FFAR4) is predicted to be a G-protein coupled cell surface receptor, containing seven transmembrane domains (as well as an extracellular portion) involved in the detection of specific fatty acids, and the G-protein associated intracellular portion involved in signal transduction. GPR120 is thought to bind medium to long-chain fatty acids, such as oleic acid and linoleic acid, in their free form. It has been predicted that two isoforms (splice variants) of the GP120 receptor exists in humans, GPR120L and GPR120S, on colonic endocrine cells. It has been suggested that the long isoform does not signal functionally in the perception of taste.

GPR120 is expressed in various mammalian tissue, and has been known to be involved in the stimulation of cholecystokinin (CCK) secretion from STC-1 an intestinal secretory cell line, in addition it has been reported that GPR120 has stimulatory effects on the secretion of glucogon-like peptide (GLP-1). GPR120 is also expressed in the pituitary gland and therefore its potential involvement in stress regulation has also been explored. GPR120 is a known receptor for unsaturated long chain fatty acids and is involved in GLP-1 secretion, insulin sensitisation and anti-inflammatory and anti-obesity effects. It has been suggested that GPR120 agonists or antagonists could be useful as potential therapeutics for the treatment of various metabolic diseases, such as diabetes. However, GPR120 has yet to be explored for its potential palatability enhancing effects.

EP 1688138A1 (Takeda Pharmaceutical Company Limited) is a European patent application directed towards a specific agent for regulating human derived 14273 receptor (GPR120 receptor) function. The document describes low molecular weight synthetic agonists or antagonists for stimulating GPR120. These substances are stated to be useful for the treatment of over-eating, diabetes, or obesity. Alternative agents capable of suppressing GPR120 are described and their use in the treatment of anorexia. The application is limited to human and mouse GPR120 receptors and relates to the identification and use of compounds in a therapeutic context.

Patent application publication WO 2007/134613 (RheoScience A/S) relates to GPR120 receptor expression in various mammalian tissues. The application suggests the use of a compound for modulating the expression of GPR120 in order to treat, alleviate, prevent or diagnose diabetes and/or obesity i.e. therapeutic applications in humans.

European patent application EP 1932920A1 (Eisai R&D Management Co Ltd) discloses a method for determining whether a substance alters human GPR120 mediated cell stimulating activity for therapeutic applications.

Patent application publication WO 2011/159297A1 (Metabolex Inc) describes human and rat GPR120 agonists and their use in the treatment of metabolic diseases including diabetes and diseases associated with poor glycaemic control. This application describes that GPR120 agonists were administered to mice to determine the effects on secretion of insulin, glucogon-like peptide 1 and various other hormones. It was shown that GPR120 agonists can lower blood glucose in response to an intra peritoneal glucose challenge in mice.

Bharat Shimpukade et al (Journal of Medicinal Chemistry, Discovery of a Patent and Selective GPR120 Agonist, 2012 May 10; 59(9):4511-4515) disclose a human GPR120 agonist for therapeutic use.

Qi Sun et al (Molecular Pharmacology, Structure-Activity Relationships of GPR120 Agonists Based on a Docking Simulation, 2010 November; 78(5):804-810) describe human GPR120 agonists for therapeutic purposes.

Takafumi Hara et al (Naunyn-Schmied Arch Pharmacol, Novel Selective Ligands for Free Fatty Acid Receptors GPR120 and GPR40, 2009 September; 380(3):247-255) attempt to identify new therapeutic ligands for human GPR120 receptor. However, the authors were only able to identify partial agonists.

Takayoshi Suzuki et al (Journal of Medicinal Chemistry, Identification of G Protein-Coupled Receptor 120-Selective Agonists Derived from PPARγ Agonists, 2008 Dec. 11; 51(23):7640-7644) describe the need to discover GPR120 selective agonists as they can be used as therapeutic agents.

CD36 (also known a FAT, GP3B, GP4, GPIV, SCARB3, thrombospondin receptor) does not belong to the G-protein coupled receptor family (it belongs to the class B scavenger receptor family), which is unusual with reference to other known fatty acid taste receptors in humans.

Domestic feline animals are known to be fussy with food, and many owners perceive that the cat will only eat certain food stuffs on certain days. Therefore, the ability to ensure that a cat responds well to a particular foodstuff would ensure the consistent acceptance of a foodstuff by an animal, and also to ensure that the owner perceives that the animal is happy and healthy.

Canine animals can also be fussy or in the case of some animals, indiscriminate in food selection. By improving the taste perception of foodstuff, canine animals can be encouraged to eat a particular foodstuff more reliably and consistently.

Currently, cats' and dogs' preference for taste stimuli are identified through feeding tests, which can be inefficient in terms of cost, time and results. Furthermore, the identification of novel taste stimuli is difficult, as many compounds may need to be tested and worked through using animal preference tests, in order to determine which may be reliably attractive to the feline and canine animals. Relatively large amounts of each test compound are necessary for such methods.

Therefore, there is a need for reliable, more efficient screening methods for identifying taste compounds that can bind to and stimulate (or otherwise modulate) certain taste receptors in animals, canine and feline animals in particular.

BRIEF SUMMARY OF THE INVENTION

The presently disclosed subject matter provides a method for identifying a compound that binds to and/or modulates the activity of a polypeptide comprising; (i) the sequence of a feline or canine GPR120 or a feline or canine CD36 receptor; (ii) the amino acid sequence as set out in SEQ ID NO:1, SEQ ID NO:3, SEQ ID NO:5, or SEQ ID NO:7; (iii) an amino acid sequence having at least 90% identity to SEQ ID NO:1 or SEQ ID NO:3; (iv) an amino acid sequence having at least 90% identity to SEQ ID NO:5 or SEQ ID NO:7; (v) an amino acid sequence comprising amino acids 127 to 279 of SEQ ID NO:3 or SEQ ID NO:7; (vi) a functional fragment of (i), (ii), (iii), (iv) or (v). the method comprising determining whether a test compound binds to and/or modulates the activity of the polypeptide.

The presently disclosed subject matter further provides a method for identifying a taste compound that binds to and/or modulates the activity of (a) GPR120 receptor and/or a CD36 receptor, wherein: a) the GPR120 receptor is: i) feline, canine or human; ii) has the amino acid sequence of SEQ ID NO:1, SEQ ID NO:5 or SEQ ID NO:9; or iii) is at least 87% identical to SEQ ID NO:1, SEQ ID NO:5 or SEQ ID NO:9; and b) the CD36 receptor is: i) feline, canine or human; ii) has the amino acid sequence of SEQ ID NO:3, 7 or 11; iii) is at least 83% identical to SEQ ID NO: 3, 7 or 11.

In certain embodiments, the method is an in vitro method. In certain embodiments, the method is an in silico method.

In certain embodiments, the in vitro method comprises: (i) measuring the biological activity of the polypeptide in the absence and in the presence of a compound; and (ii) identifying a compound as one which binds to or modulates the biological activity of the polypeptide, when there is a difference between the biological activity in the absence, compared to the presence of the compound. In certain embodiments, the in vitro method further comprises contacting the polypeptide with a compound.

In certain embodiments, the in silico method comprises: (a) predicting the 3-dimensional (3D) structure of the polypeptide; (b) screening the predicted 3D structure of the polypeptide in silico with a 3D structure of a test compound; (c) determining if the test compound fits a binding site of the polypeptide; and (d) identifying a compound as one which binds to and modulates the biological activity of the polypeptide, when the 3D structure of the compound fits the binding site of the 3D structure of the polypeptide.

The presently disclosed subject matter further provides a foodstuff comprising an agent or compound identified by the method of anyone of the methods disclosed herein.

The presently disclosed subject matter further provides a kit for determining whether a compound or agent activates a polypeptide comprising; (i) the sequence of a feline or canine GPR120 or a feline or canine CD36 receptor; (ii) the amino acid sequence as set out in SEQ ID NO:1, SEQ ID NO:3, SEQ ID NO:5, or SEQ ID NO:7; (iii) an amino acid sequence having at least 90% identity to SEQ ID NO:1 or SEQ ID NO:3; (iv) an amino acid sequence having at least 90% identity to SEQ ID NO: 5 or SEQ ID NO:7; (v) an amino acid sequence comprising amino acids 127 to 279 of SEQ ID NO:3 or SEQ ID NO:7; (vi) a functional fragment of (i), (ii), (iv) or (v). the kit comprising one or more polypeptides of (i) to (vi) and one or more test compounds.

The presently disclosed subject matter further provides an isolated polypeptide comprising the amino acid sequence as set out in SEQ ID NO:3, and an isolated nucleic acid encoding a polypeptide comprising the amino acid sequence as set out in SEQ ID NO:3. In certain embodiments, the isolated nucleic acid comprising the nucleotide sequence of SEQ ID NO:4.

The presently disclosed subject matter further provides a vector comprising the nucleic acids disclosed herein, and a host cell containing the polypeptides the nucleic acids, or the vectors disclosed herein.

The presently disclosed subject matter further provides a fusion protein comprising a polypeptide comprising; (i) the sequence of a feline or canine GPR120 or a feline or canine CD36 receptor; (ii) the amino acid sequence as set out in SEQ ID NO:1, SEQ ID NO:3, SEQ ID NO:5, or SEQ ID NO:7; (iii) an amino acid sequence having at least 90% identity to SEQ ID NO:1, SEQ ID NO:3; (iv) an amino acid sequence having at least 90% identity to SEQ ID NO: 5 or SEQ ID NO:7; (v) an amino acid sequence comprising amino acids 127 to 279 of SEQ ID NO:3 or SEQ ID NO:7; (vi) a functional fragment of (i), (ii), (iii), (iv) or (v).

BRIEF DESCRIPTION OF THE DRAWINGS

FIG. 1 shows the amino acid sequence of feline GPR120.
FIG. 2 shows the nucleotide sequence of feline GPR120.
FIG. 3 shows the amino acid sequence of feline CD36.
FIG. 4 shows the nucleotide sequence of feline CD36.
FIG. 5 shows the amino acid sequence of canine GPR120.
FIG. 6 shows the nucleotide sequence of canine GPR120.
FIG. 7 shows the amino acid sequence of canine CD36.
FIG. 8 shows the nucleotide sequence of canine CD36.
FIG. 9 shows the amino acid sequence of human GPR120.
FIG. 10 shows the nucleotide sequence of human GPR120.
FIG. 11 shows the amino acid sequence of human CD36.
FIG. 12 shows the nucleotide sequence of human CD36.
FIG. 13 shows the sequence difference between SEQ ID NO:3 and published feline CD36 sequences.
FIG. 14 shows a feline dose response curve for oleic acid.
FIG. 15 shows a feline dose response curve for linoleic acid.
FIG. 16 shows a feline dose response curve for lauric acid.
FIG. 17 shows a feline dose response curve for palmitic acid.
FIG. 18 shows canine response curves for linoleic acid.
FIG. 19 shows canine response curves for oleic acid.
FIG. 21 shows the predicted structure of human CD36.
FIG. 22 shows feline GPR120 transient transfections in a stable cell line.
FIG. 23 shows feline GPR120 transient transfections in CHOK1 cells.
FIG. 24 shows free fatty acid dose response curves and $EC_{50}$ values obtained using an in vitro assay for feline GRP120.
FIG. 25 shows free fatty acid dose response curves and corresponding $EC_{50}$ values obtained using in vitro assay for feline GPR120 alone and co-transfected with CD36.
FIG. 26 shows fluorescence response for cat CD36 only in the presence of SSO, an antagonist of CD36.
FIG. 27 shows a schematic of linoleic acid in the binding site of GPR120 using an in silico method.
FIG. 28 shows a schematic of oleic acid in the binding site of GPR120 using an in silico method.

DETAILED DESCRIPTION OF THE INVENTION

Figure 20:
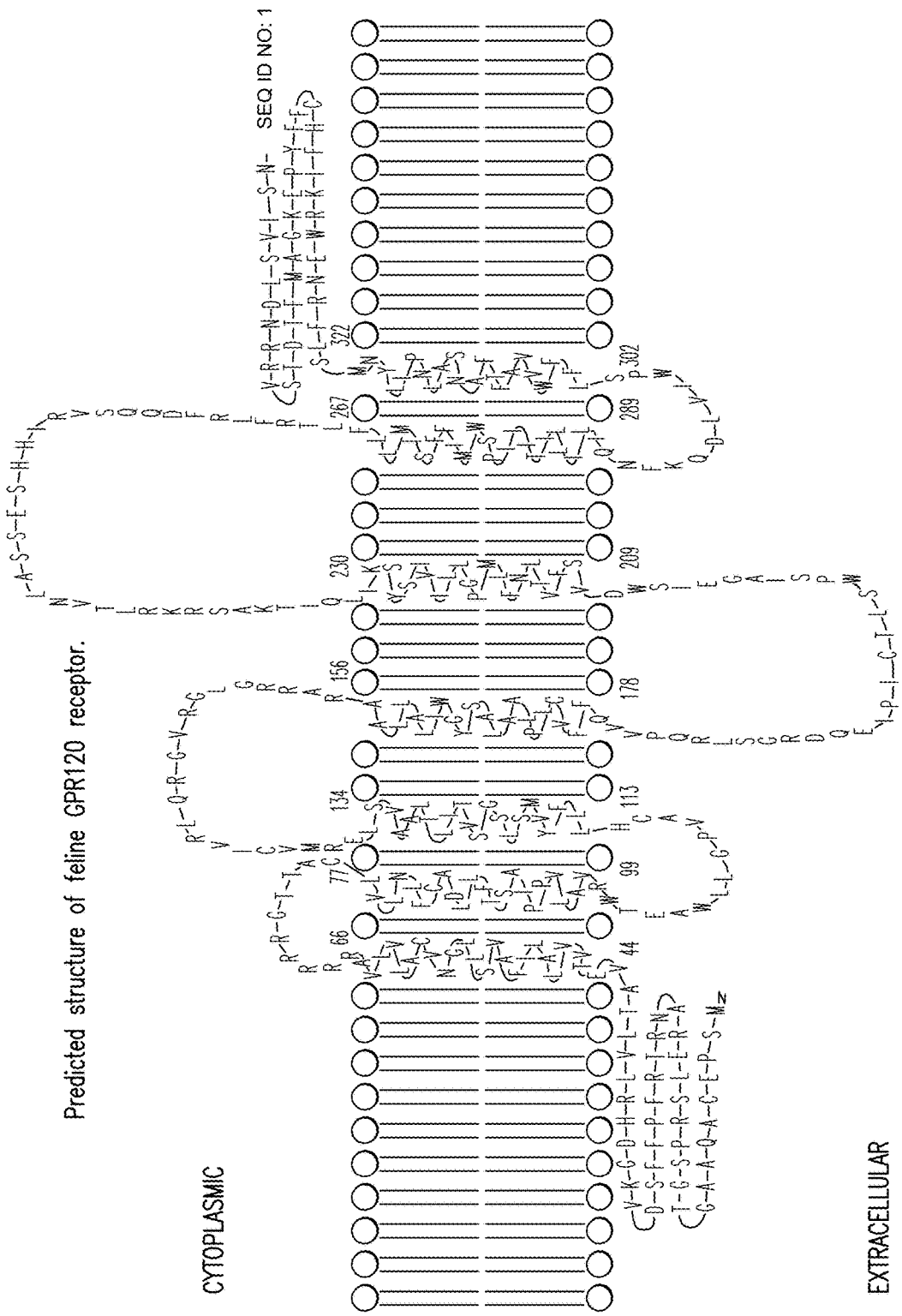
FIG. 20 shows the predicted structure of feline GPR120.

Therefore, in one aspect, the present invention provides a method for identifying a compound that binds to and/or modulates the activity of a polypeptide, the polypeptide comprising;
(i) the sequence of a feline or canine GPR120 or a feline or canine CD36 receptor;
(ii) the amino acid sequence as set out in SEQ ID NO:1, SEQ ID NO:3, SEQ ID NO:5, SEQ ID NO:7;
(iii) an amino acid sequence having at least 90% identity to SEQ ID NO:1 or SEQ ID NO:3;
(iv) an amino acid sequence having at least 90% identity to SEQ ID NO:5 or SEQ ID NO:7;
(v) an amino acid sequence comprising amino acids 127 to 279 of SEQ ID NO:3 or SEQ ID NO:7; or
(vi) a functional fragment of (i), (ii), (iii), (iv) or (v) the method comprising determining whether a test compound binds to and/or modulates the activity of the polypeptide.

The inventors have found that polypeptides comprising the sequence of SEQ ID NO: 1 and SEQ ID NO:3 are amino acid sequences of the feline homologues of the human GPR120 and CD36 fatty acid receptors, respectively. SEQ ID NO:5 and SEQ ID NO:7 are the amino acid sequences of the canine GPR120 and CD36 receptors, respectively. The human sequences are shown in SEQ ID NO:9 and SEQ ID NO: 11, respectively.

The sequences were obtained from feline or canine re-sequenced genomic DNA and compared to human sequences and to suggested predicted feline and canine sequences. Some differences were found in the feline CD36 gene sequence, between that published and that isolated by the inventors. Also included in the invention is the use of functional and allelic variants, which may differ in sequence but remain able to be stimulated by fatty acids, and lead to the perception of fatty acids by the animal and as such, within a screening method.

The feline and canine sequences are predicted to be active, functional receptors, due to the sequence similarity to the human, rat and murine GPR120 and CD36 sequences that are available (at least 82% similarity). There is no reason not to believe that such receptors are not functional in vivo, particularly in view of the fact that the inventors have shown a clear response to feline and canine animals to oleic and linoleic acid, which are known to bind to the equivalent human receptors, and in vitro assays show binding and responses of these receptors to known ligands.

Thus, in an aspect of the invention, the method is an in vitro method. The in vitro method may comprise:
Measuring the biological activity of the polypeptide in the absence and in the presence of a test compound; and
Identifying an agent as one which binds to or modulates the biological activity of the polypeptide, when there is a difference between the biological activity in the absence compared to the presence of the test agent.

The in vitro method may further comprise contacting the polypeptide with a test compound.

Detection methods for use in the method may include the use of a labelled compound/agent, and after washing determining which test compounds remain bound to the receptors. Detecting activity induced by the binding of a compound to the receptor may be by way of monitoring the free calcium concentration within the cell which increases as a result of receptor activation known as calcium flux, as well known to a person skilled in the art. Monitoring may be by way of fluorescence detection, such as a calcium sensitive fluorescent dye, or luminescence detection, using a luminescent protein. An alternative method involves cGMP activity monitoring as also known by the skilled person.

The region between amino acid residues 127 and 279 of CD36 has been implicated in long chain fatty acid binding in humans, and thus, a polypeptide comprising this portion of SEQ ID NO:3 or SEQ ID NO:5 may be used in a method of the invention. A polypeptide comprising amino acid residues 155 to 183 of SEQ ID NO:3 or SEQ ID NO:5 may be used in a screening method of the invention.

The method may also involve the use of two polypeptides of the invention at the same time, since the CD36 protein may act as a chaperone in order to allow a compound or agent to interact with the protein of GPR120 or to increase the interaction between GPR120 and the fatty acid or other activating compound. Thus, an in vitro method comprising both polypeptides is included as a further aspect of the invention. As such, the invention includes a method comprising measuring the biological activity of a GPR120 polypeptide (SEQ ID NO:1 or SEQ ID NO:5) or a fragment thereof in the presence of a CD36 polypeptide (SEQ ID NO:3 OR SEQ ID NO:7 respectively) in the absence and in the presence of a test compound; and identifying such an agent that causes a difference in activity compared to the activity in the absence of the agent.

Methods of screening for agents which can modulate a biological activity of a polypeptide are well known in the art, and may involve the use of solid supports to which polypeptides of the invention are immobilised.

Agents identified by such screening methods may inhibit/antagonise or activate/agonise the biological activity of a peptide of the invention. Thus, such agents may be useful as receptor agonists or antagonists.

Compounds identified by the in vitro method of the invention may be further tested in vivo, for example, in feeding tests.

The invention also relates to a method for identifying a taste compound that binds to and/or modulates the activity of a GPR120 receptor and/or a CD36 receptor, wherein the GPR120 or CD36 receptor is feline, canine or human (SEQ ID NOs: 1, 3, 5, 7, 9 or 11) or wherein the GPR120 receptor is at least 87% identical to SEQ ID NO: 1, and wherein the CD36 receptor is at least 82% identical to SEQ ID NO:3.

The GPR120 receptor may be 90%, 91%, 92%, 93%, 94%, 95%, 96%, 97%, 98%, 99% identical to any of SEQ ID NOs: 1, 5 or 9.

The CD36 receptor may be 85%, 90%, 91%, 92%, 93%, 94%, 95%, 96%, 97%, 98%, 99% to any of SEQ ID NOs: 3, 7 or 11.

The identification of such taste compounds may result in more palatable foodstuff additives for cat, dog or human consumption.

It is desirable to identify compounds that are more beneficial than compounds already known to bind to GPR120 and/or CD36; examples include compounds that are easier/more cost effective to produce; compounds that can be used in smaller quantities for similar effects to known compounds; compounds that interact synergistically with other compounds.

The invention may also concern the receptors known as FFAR1 (GPR40), FFAR2 (GPR43) and/or FFAR3 (GPR41). These polypeptides have been described previously as binding to fatty acids, but neither in the context of taste compounds, nor in the context of feline and canine animals.

Methods as herein described for identifying compounds that bind to and/or modulate the biological activity of FFAR1, 2 or 3 receptors are therefore also included within the scope of the invention.

All features of each aspect apply to each other aspect mutatis mutandis.

Amino acid sequences are described herein using the standard single letter code. The sequences are described in the direction from the N-terminus to the C-terminus from left to right. The amino acids which can be incorporated into the peptides include any of the known naturally occurring amino acids.

In addition, the peptides of the invention may also include modified amino acids, that is, amino acids which do not naturally occur in nature. For example, the peptides of the invention may include norleucine, or other modified amino acids known in the art.

The peptides of the invention may consist only of the amino acid sequences disclosed herein, or may comprise other amino acids in addition to those sequences. The polypeptide sequences described herein may contain additional amino acids at the N-terminal (the amino terminal) end and/or at the C-terminal (the carboxy terminal) end of the sequences, particularly when used in a screening method of the invention. Such additional amino acids may assist with immobilising the polypeptide for screening purposes, or allow the polypeptide to be part of a fusion protein, for ease of detection of biological activity.

The polypeptides of the invention include homologues or derivatives of the above sequences, which retain the ability to bind medium to long chain fatty acids. A large number of conservative amino acid substitutions can be introduced into the peptide without causing any significant structural or functional changes. Thus, it may be possible to replace one amino acid with another of similar "type", for instance, replacing one hydrophobic amino acid with another. Suitable conservative amino acid substitutions are known in the art. In the case of such homologues and derivatives, the degree of identity with the specific sequences identified herein is less important than that the homologue or derivative should retain the ability to bind a fatty acid and for a signal to be transmitted downstream. However, suitably, homologues or derivatives having at least 90% identity to the sequences provided herein are provided. Most preferably, homologues or derivatives having at least 91%, 92%, 93%, 94%, 95%, 96%, 97%, 98% or 99% identity are provided.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. The NBLAST and XBLAST programs of Altschul, et al. (1990) *J. Mol. Biol.* 215:403-410 have incorporated such an algorithm. BLAST nucleotide searches can be performed with the NBLAST program, score=100, wordlength=12, to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilised as described in Altschul et al. (1997) *Nucleic Acids Res.* 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. See http://www.ncbi.nlm.nih.gov. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) *Comput. Appl. Biosci.*, 10:3-5; and FASTA described in Pearson and Lipman (1988) *Proc. Natl. Acad. Sci.* 85:2444-8. Within FASTA, ktup is a control option that sets the sensitivity and speed of the search.

Experiments with the human and rodent GPR120 and CD36 proteins have been carried out with linoleic acid and oleic acid, many of them with knock-out rodent models. While these show the effect of lacking the receptor they do not specifically show that the molecule activates the receptor. An example showing oleic and linoleic acid responses in vitro for Human GPR120 experiments in vitro is described in Galindo et al 2011 Chem. Sen. Human CD36 experiments are described in (Kuda et al 2013 J. Biol. Chem), in relation to linoleic acid. Cartoni et al, 2010 J. Neurosci. showed that GPR120 knock-out mice had altered responses to linoleic and oleic acid. Gaillard et al (2008, FASEB) showed that mouse CD36+ taste receptor cells were sensitive to linoleic acid while CD36– taste cells were not. The human and rodent homologues of the polypeptides described herein have been shown to bind to these specific long chain fatty acids. The feline and canine equivalent sequences appear to bind to such molecules in view of the in vivo response to fatty acids at increasing concentrations, as shown herein. Furthermore, herein described in vitro assays with the feline receptors show a positive activation by linoleic and oleic acid.

The peptides for use in the screening methods of the invention may be produced by chemical synthesis methods well known in the art. For example, the peptides may be synthesized chemically, using solid phase peptide synthesis. These methods employ either solid or solution phase synthesis methods (see for example, J. M. Stewart, and J. D. Young, Solid Phase Peptide Synthesis, 2nd Ed., Pierce Chemical Co., Rockford III. (1984) and G. Barany and R. B. Merrifield, The Peptides: Analysis Synthesis, Biology editors E. Gross and J. Meienhofer Vol. 2 Academic Press, New York, 1980, pp. 3-254 for solid phase synthesis techniques; and M Bodansky, Principles of Peptide Synthesis, Springer-Verlag, Berlin 1984, and E. Gross and J. Meienhofer, Eds., The Peptides: Analysis, Synthesis, Biology, supra, Vol 1, for classical solution synthesis). Other peptide synthesis methods are known in the art.

Alternatively, the peptides may be produced by expressing nucleic acid molecules encoding precursors of the peptides. In another aspect, the invention provides a nucleic acid sequence encoding a precursor of the peptides of the invention. Such nucleic acids can be synthesised by methods which are well known in the art (for example, see *Molecular Cloning: A Laboratory Manual:* 3$^{rd}$ Edition Sambrook and Russell, 2001, Cold Spring Harbor Laboratory Press).

In addition, peptide-encoding nucleic acids may be incorporated in a suitable nucleic acid vector. In a further aspect, the invention provides a vector comprising the nucleic acid of the invention. The vector may have a promoter element operably linked to the peptide-encoding nucleic acid sequence. Suitable vectors and methods of producing such vectors are known in the art.

The nucleic acid of the invention or vector of the invention may be introduced into a host cell. Accordingly, in an additional aspect, the invention provides a cell comprising the nucleic acid or vector of the invention. The cell may be an isolated cell, such as a CHO K1 cell, or other suitably known stable cell line.

In a further aspect, the present invention provides fusion proteins including the polypeptides described herein. Such fusion proteins may contain a detectable marker, a functional group such as a carrier, a label, a stabilising sequence or a mechanism by which fatty acid binding may be detected. Suitable labels include a FLAG tag, His tag, MYC tag, a maltose binding protein and others known in the art. The invention also provides nucleic acids encoding such fusion proteins, vectors containing fusion protein-encoding nucleic acids, and host cells comprising such nucleic acids or vectors.

Methods of synthesising such fusion proteins are well known in the art.

The method of the invention may be an in silico method. Such a method may comprise:
(i) predicting the (3-dimensional) 3D structure of the polypeptide;
(ii) screening the predicted 3D structure of the polypeptide in silico with a test compound;
(iii) predicting whether the test compound interacts with the binding site of the polypeptide; and
(iv) identifying a compound as one that binds to and modulates the biological activity of the polypeptide when the 3D structure of the compound fits the binding site of the 3D structure of the polypeptide.

Such techniques and methods are known in the art to the skilled person. Models of GPR120 were built using crystal structures of other Group A GPCRs as templates for homology modelling that were available from the Protein Data Bank, as would normally be performed by someone skilled in the art. The Modeler software package was used. Simulations and minimizations for individual free fatty acids (e.g. linoleic acid) were performed, as would normally be performed by someone skilled in the art. Any suitable modelling software package may be used, as can suitable simulation software programs.

A compound identified by the in silico screen of the invention as binding to GPR120 or to CD36 may be further tested by the in vitro method of the invention. Additionally or alternatively such a compound may be tested in vivo, for example, in feeding tests.

A further aspect of the invention provides compounds that modulate the biological activity of a GPR120 receptor or a CD36 receptor, in accordance with the first aspect of the invention.

The method of this aspect of the invention is therefore a suitable screening method for identifying taste compounds that may be used in a foodstuff for a feline or canine animal to ensure long term acceptance and consistent ingestion of such a foodstuff.

Thus, in an additional aspect, the invention provides a foodstuff comprising an agent or compound identified by the method of the invention.

The foodstuff may be any known in the art. A compound identified by the method of the invention may be incorporated into any product which a feline or canine may consume in its diet. Thus, the invention covers standard food products, supplements, pet food, drinks, snacks and treats. The food product is preferably a cooked product. It may incorporate meat or animal derived material (such as beef, chicken, turkey, lamb, blood plasma, marrowbone etc., or two or more thereof). The food product alternatively may be meat free (preferably including a meat substitute such as soya, maize gluten or a soya product) in order to provide a protein source. The product may contain additional protein sources such as soya protein concentrate, milk proteins, gluten etc. The product may also contain a starch source, such as gelatinised starch, such as one or more grains (e.g. wheat, corn, rice, oats, barely etc.) or may be starch free. A typical dry commercial cat food contains about 10-70% crude protein, about 10-60% fat and the remainder being carbohydrate, including dietary fibre and ash. A typical wet or moist product contains (on a dry matter basis) about 40% fat, 50% protein and the remainder being fibre and ash. The present invention is particularly relevant for a pet foodstuff as herein described which is sold as a diet, foodstuff or supplement for a cat or a dog. In the present text the term "domestic" cat mean cats, in particular *Felis domesticus* (*Felis catus*) and the term "domestic" dog means dogs, in particular *Canis lupus familiaris*. Preferably, the pet foodstuff will meet the macronutrient requirements of the animal.

Preferred features of each aspect of the invention are as for each of the other aspects, mutatis mutandis.

All referenced documents are disclosed herein by the fullest extent permitted by law.

EXAMPLES

The invention will now be described with reference to the following non-limiting examples. Reference is made to the accompanying figures.

Example 1

Determining the Correct Sequence of Feline GPR120.

DNA was collected from 26 cats using cheek swabs. Two swabs were collected from each cat. DNA extracted with the Qiagen DNeasy Blood and Tissue Kit was used for sequencing. Primers were designed to flank exonic regions based on the publicly available feline genome sequence. All exonic regions were sequenced in both directions where possible. Sequences were analysed using Sequencher v5.1 (Gene Codes, USA). Consensus sequences from the 26 cats were compared with the publicly available sequence and a final consensus sequence for all exons was generated.

These sequences are based on re-sequenced WCPN cat data with reference to RNA-Seq data and publicly available sequences for cat and human.

The confirmed fGPR120 coding sequence matches the sequence on Ensembl. This is the correct isoform as the other long isoform identified in humans does not signal functionally.

Example 2

Determining the Correct Sequence of Feline CD36.

DNA was collected from 26 cats using cheek swabs. Two swabs were collected from each cat. DNA extracted with the Qiagen DNeasy Blood and Tissue Kit was used for sequencing. Primers were designed to flank exonic regions based on the publicly available feline genome sequence. All exonic regions were sequenced in both directions where possible. Sequences were analysed using Sequencher v5.1 (Gene Codes, USA). Consensus sequences from the 26 cats were compared with the publicly available sequence and a final consensus sequence for all exons was generated.

These sequences are based on re-sequenced WCPN cat data with reference to RNA-Seq data, cDNA sequencing data from feline taste buds and publicly available sequences for cat and human.

The transcript sequences available on Ensembl for both human and cat contain sections after the first stop codon. It is likely that in the cat, as is the case for human, the first portion of the transcript sequence up to the first stop codon is the primary coding sequence. At position 300 there is a run of 8 adenine residues. This differs from the predicted transcript on Ensembl but results in a 472 amino acid protein which matches the length of the other isoform in cat and matches the length of the human protein. Therefore neither of the transcripts predicted on Ensembl match this sequence exactly but sequencing of cDNA from cat taste papillae shows that this is the correct transcript configuration.

Example 3

Determining the Correct Sequence of Canine GPR120.

DNA was collected from 84 dogs by small volume blood sample. Whole genome sequencing using the Illumina platform was performed on all samples giving an average coverage of 15×. Data was mapped to the reference genome using Bowtie2. Regions of interest were extracted using in-house Perl scripts. Exonic regions were identified and a final consensus sequence for all exons was generated.

These sequences are based on genome sequencing dog data with reference to RNA-Seq data and publicly available sequences for dog and human.

The confirmed canine GPR120 coding sequence matches the sequence on Ensembl.

Example 4

Determining the Correct Sequence of Canine CD36.

DNA was collected from 84 dogs by small volume blood sample. Whole genome sequencing using the Illumina platform was performed on all samples giving an average coverage of 15×. Data was mapped to the reference genome using Bowtie2. Regions of interest were extracted using in-house Perl scripts. Exonic regions were identified and a final consensus sequence for all exons was generated.

These sequences are based on genome sequencing dog data with reference to RNA-Seq data and publicly available sequences for dog and human.

The confirmed canine CD36 coding sequence matches the sequence on Ensembl.

Example 5

Feeding Test to Determine Feline Response to Oleic Acid.

A cat gel panel was used to compare the palatability of a range of concentrations of oleic acid in a monadic exposure. The dose response tested 8 concentrations of oleic acid ranging from 0.001% oleic acid to 1% oleic acid. All products (including the blank, 0% oleic acid) contained 25 mM L-histidine as an ingestive/positive tastant to increase the baseline gel intake, enabling the identification of a potential negative impact of the oleic acid concentration.

Oleic acid concentrations of 0.1%, 0.2%, 0.3%, and 0.6% (w/v) had a significantly higher intake compared to the blank (0% oleic acid), showing that cats were able to taste the linoleic acid.

Example 6

Feeding Test to Determine Feline Response to Linoleic Acid.

A cat gel panel was used to compare the palatability of a range of concentrations of linoleic acid in a monadic exposure. The dose response tested 8 concentrations of linoleic acid ranging from 0.001% linoleic acid to 1% linoleic acid. All products (including the blank, 0% linoleic acid) contained 25 mM L-histidine as an ingestive/positive tastant to increase the baseline gel intake, enabling the identification of a potential negative impact of the linoleic acid concentration.

The linoleic acid concentration of 0.1% (w/v) had a significantly higher intake compared to the blank (0% linoleic acid). There was a trend for the higher concentrations to become aversive/negative, with a reduced intake compared to the blank (0% linoleic acid), showing that cats were able to taste the linoleic acid.

Example 7

Feeding Test to Determine Feline Response to Lauric Acid.

A cat gel panel was used to compare the palatability of a range of concentrations of lauric acid in a monadic exposure. The dose response tested 5 concentrations of lauric acid ranging from 0.05% lauric acid to 1% lauric acid. All products (including the blank, 0% lauric acid) contained 25 mM L-histidine as an ingestive/positive tastant to increase the baseline gel intake, enabling the identification of a potential negative impact of the lauric acid concentration.

The lauric acid concentration of 0.1% had the highest intake overall compared to the blank (0% lauric acid). However, the highest concentrations tested of 0.6% and 1% lauric acid were significantly aversive/negative compared to the blank (0% lauric acid), also showing that cats were able to taste the lauric acid.

Example 8

Feeding Test to Determine Feline Response to Palmitic Acid.

A cat gel panel was used to compare the palatability of a range of concentrations of palmitic acid in a monadic exposure. The dose response tested 5 concentrations of palmitic acid ranging from 0.05% palmitic acid to 1% palmitic acid. All products (including the blank, 0% palmitic acid) contained 25 mM L-histidine as an ingestive/positive tastant to increase the baseline gel intake, enabling the identification of a potential negative impact of the palmitic acid concentration.

There was no significant difference in the intake of any of the palmitic acid concentrations tested, due to the fact that it is solid at room temperature (melting temperature approximately 63° C.). Therefore, the palmitic acid was not able to interact and bind with the fatty acid receptors to produce a taste response by the cats.

Example 9

Feeding Test to Determine Canine Response to Linoleic Acid.

Two different dog panels were used to compare the palatability of concentrations of linoleic acid. Each panel was made up of a single breed of dog; each panel being a different breed. The canine panels were used to compare the palatability of a range of concentrations of linoleic acid in a monadic exposure. The dose response tested 3 concentrations of linoleic acid ranging from 0.01% linoleic acid to 1% linoleic acid. All products (including the blank, 0% linoleic acid) contained 100 mM L-histidine as an ingestive/positive tastant to increase the baseline gel intake, enabling the identification of a potential negative impact of the linoleic acid concentration.

The different breeds demonstrated different responses to linoleic acid. Breed 1 had a significant positive/ingestive response for linoleic acid at the highest concentration tested of 1% compared to the blank (0% linoleic acid), while Breed 2 had smaller differences between the linoleic acid concentrations tested.

Example 10

Feeding Test to Determine Canine Response to Oleic Acid.

Two different dog panels were used to compare the palatability of concentrations of oleic acid. Each panel was made up of a single breed of dog; each panel being a different breed.

The canine panels were used to compare the palatability of a range of concentrations of oleic acid in a monadic exposure. The dose response tested 3 concentrations of oleic acid ranging from 0.01% oleic acid to 1% oleic acid. All products (including the blank, 0% oleic acid) contained 100 mM L-histidine as an ingestive/positive tastant to increase the baseline gel intake, enabling the identification of a potential negative impact of the oleic acid concentration.

The different breeds both demonstrated a response to oleic acid. Breed 1 had a significant positive/ingestive response for oleic acid at the highest concentration tested of 1% compared to the blank (0% oleic acid), while breed 2 had a significant positive/ingestive response for oleic acid at 0.1% compared to the blank (0% linoleic acid). This data shows that the dogs were able to taste the oleic acid.

Example 11

Method for GP120 and GPR120+CD36 Receptor In Vitro Assays Development and Use.

Initially the gene sequences for the target receptors GPR120 and CD36 were confirmed by re-sequencing the genes of cats and dogs.

In the case of GPR120 (FFAR4, O3FAR1) the sequences obtained were compared with the currently available feline or canine reference sequence and the human reference sequence. Sequences for the short isoform were used.

In the case of CD36 the sequences obtained were compared with the currently available feline or canine reference sequence and the human reference sequence.

Once target sequences were established they were synthesised and cloned into the expression vectors pcDNA3.1Hygro and pcDNA3.1G418. These constructs were then transiently transfected into the CHO K1 immortalised cell line, and other commonly used cell lines using Lipofectamine 2000 and testing was performed to establish the successful expression of the target protein. The testing was carried out using a calcium sensitive fluorescent dye (Fluo8). Transfected cells were seeded into 384 well assay plates. By loading the cells with the dye and then challenging the cells with an agonist for the receptor the response of the cells could be recorded on the FLIPR$^{TETRA}$ instrument by measuring the increase in fluorescence associated with intracellular calcium release, thus confirming the functional expression of the receptor. Suitable experimental controls eliminate any possibility that the response of the cells is non-specific or that the fluorescence increase is due to factors other than the release of intracellular calcium by the cells.

Both human and cat GPR120 showed specific responses to fatty acids in the micro-molar range when transiently expressed in the stable cell line A or CHOK1 cell line (FIG. 22 and FIG. 23, respectively). The human receptor did not require the presence of an exogenous G-protein but the cat receptor did require this in the stable cell line A. Dose response curves were generated for all the compounds tested (FIG. 24) and $EC_{50}$ values were calculated. The effect of co-transfection of GPR120 and CD36 is shown in FIG. 25.

Example 12

Method for CD36 Receptor In Vitro Assay Development and Use.

Initially the gene sequence for the target receptor CD36 was confirmed by re-sequencing the genes of cats and dogs.

The CD36 sequences obtained were compared with the currently available feline or canine reference sequence and the human reference sequence.

Once target sequence was established it was synthesised and cloned into the expression vectors pcDNA3.1Hygro. The construct was then transiently transfected into the CHO K1 immortalised cell line and other commonly used cell lines using Lipofectamine 2000 and testing was performed to establish the successful expression of the target protein. The testing was carried out using a calcium sensitive fluorescent dye (Fluo8). Transfected cells were seeded into 384 well assay plates. By loading the cells with the dye and then challenging the cells with an agonist for the receptor the response of the cells could be recorded on the FLIPR$^{TETRA}$ instrument by measuring the increase in fluorescence associated with intra-cellular calcium release, thus confirming the functional expression of the receptor. Suitable experimental controls eliminate any possibility that the response of the cells is non-specific or that the fluorescence increase is due to factors other than the release of intracellular calcium by the cells.

Further experiments with CD36 were performed to establish whether the putative CD36 antagonist Sulfo-N-succinimidyl Oleate (SSO) would inhibit CD36 mediated calcium influx after pre-treatment with Thapsigargin. The response of cells transfected with CD36 or a mock control are shown in FIG. 28.

Example 13

Method for GPR120 Receptor in Silico Model Development and Use.

Models of GPR120 were built using crystal structures of Group A GPCRs as templates for homology modelling that were available from the Protein Data Bank. The Modeler software package was used.

Simulations and minimizations for individual free fatty acids (e.g. linoleic acid) were performed. The program Charmm in Discovery Studio was used.

What is claimed is:

1. A method for increasing palatability of a pet foodstuff comprising:
    (a) contacting a polypeptide with a compound, wherein the polypeptide comprises GPR120 comprising the amino acid sequence set forth in SEQ ID NO:5,
    (b) measuring the biological activity of the polypeptide in the absence and in the presence of the compound, and
    (c) admixing the compound or a composition comprising the compound with a pet foodstuff when there is a difference between the biological activity in the absence, compared to the presence of the compound, wherein the compound has an $EC_{50}$ value of no more than 110 µM.

2. A method according to claim 1, wherein the method is an in vitro method.

3. The method of claim 1, wherein the biological activity of the polypeptide is measured in a cell comprising the polypeptide and a second polypeptide comprising CD36.

4. The method of claim 1, wherein the biological activity of the polypeptide is measured in a cell comprising the polypeptide and a second polypeptide comprising an exogenous G-protein.

5. The method of claim 2, wherein the polypeptide is expressed in a cell.

6. The method of claim 5, wherein the polypeptide is expressed by a vector.

7. The method of claim 5, wherein the biological activity of the polypeptide is measured by monitoring a calcium concentration or a cGMP activity within the cell.

8. The method of claim 7, wherein the calcium concentration is monitored by fluorescence detection or luminescence detection.

9. The method of claim 8, wherein the fluorescence detection comprises a calcium sensitive fluorescent dye.

10. The method of claim 1, further comprising testing the compound in an animal feeding test.

11. The method of claim 1, wherein the compound is present at a concentration of between 0.001% and 1% in the pet foodstuff.

12. The method of claim 1, wherein the compound is present at a concentration of between 0.01% and 1% in the pet foodstuff.

* * * * *